(12) United States Patent
Davey et al.

(10) Patent No.: US 6,982,259 B2
(45) Date of Patent: Jan. 3, 2006

(54) N-HETEROCYCLIC DERIVATIVES AS NOS INHIBITORS

(75) Inventors: David D. Davey, El Sobrante, CA (US); Raju Mohan, Encinitis, CA (US); Gary B. Phillips, Pleasant Hill, CA (US); Guo Ping Wei, San Ramon, CA (US); Wei Xu, Danville, CA (US)

(73) Assignee: Schering Aktiengesellschaft, Berlin (DE)

(*) Notice: Subject to any disclaimer, the term of this patent is extended or adjusted under 35 U.S.C. 154(b) by 171 days.

(21) Appl. No.: 10/422,185

(22) Filed: Apr. 23, 2003

(65) Prior Publication Data
US 2004/0023950 A1 Feb. 5, 2004

Related U.S. Application Data
(60) Provisional application No. 60/377,274, filed on Apr. 30, 2002.

(51) Int. Cl.
*C07D 401/10* (2006.01)
*C07D 403/10* (2006.01)
*A61K 31/4164* (2006.01)
*A61K 31/454* (2006.01)
*A61P 9/04* (2006.01)

(52) U.S. Cl. .................. 514/217.08; 514/326; 514/396; 514/397; 546/210; 540/603; 548/343.5

(58) Field of Classification Search ............... 546/210, 546/207; 548/343.5; 540/603, 596; 514/217.08, 514/326, 396, 397, 212.01, 317
See application file for complete search history.

(56) References Cited

U.S. PATENT DOCUMENTS

| | | |
|---|---|---|
| 5,244,865 A | 9/1993 | Seitz et al. |
| 5,426,110 A | 6/1995 | Gossett et al. |
| 5,489,591 A | 2/1996 | Kobayashi et al. |
| 5,663,334 A | 9/1997 | Sheldrake et al. |
| 6,172,005 B1 | 1/2001 | Selby |
| 6,432,947 B1 | 8/2002 | Arnaiz et al. |
| 6,525,051 B2 | 2/2003 | Davey et al. |
| 2002/0040024 A1 * | 4/2002 | Apodaca et al. ......... 514/235.5 |

FOREIGN PATENT DOCUMENTS

| | | |
|---|---|---|
| EP | 0 257 850 A2 | 3/1988 |
| EP | 0 306 440 A2 | 3/1989 |
| EP | 0 640 599 A1 | 3/1995 |
| EP | 0 757 988 A1 | 2/1997 |
| EP | 0 949 242 A1 | 10/1999 |
| WO | WO96/14842 | 5/1996 |
| WO | WO96/14844 | 5/1996 |
| WO | WO98/09960 | 3/1998 |
| WO | WO01/14371 A1 | 3/2001 |
| WO | WO02/32897 A1 | 4/2002 |
| WO | WO03/022821 A1 | 3/2003 |

OTHER PUBLICATIONS iFons et al. Cytokine ((7) 453–462, 1997.*
Ohmori et al. J. Med. Chem. 39: 3971–3979, 1996.*
Feldman et al., "The Surprising Life of Nitric Oxide", *Chemical and Engineering News* (1993) 26–38.
Del Corona et al., "Synthesis and in vitro study of platelet antiaggregant activity of 2(4)–imidazol–1–yl–4(2)–cycloalkylaminopyrimidines", *Eur. J. Med. Chem.* (1991) 26(7):729–733.
Fujisawa et al., "Inducible Nitric Oxide Synthase in a Human Glioblastoma Cell Line", *J. Neurochem.*(1995) 64(1): 85–91.
Damiani et al., "Fluormetric Determination of Nitrite" *Talanta* (1986)33(8): 649–652.
Nathan, "Nitric oxide as a secretory product of mammalian cells", *FASEB Journal* (1992) 6:3052–3064.
Lampe et al., "A novel Rearrangement of 1–(2–Aminoaryl)imidazoles", *J. Heterocyclic Chem* (1994) 31:287–291.
Lis et al., "Synthesis of Novel (Aryloxy) propanolamines and Related Compounds Possessing Both Class II and Class III Antiarrhythmic Activity" *J. Med. Chem.* (1990) 33:2883–2891.

* cited by examiner

*Primary Examiner*—Venkataraman Balasubramanian
(74) *Attorney, Agent, or Firm*—Berlex, Inc.

(57) ABSTRACT

N-Heterocyclic derivatives of the following formula:

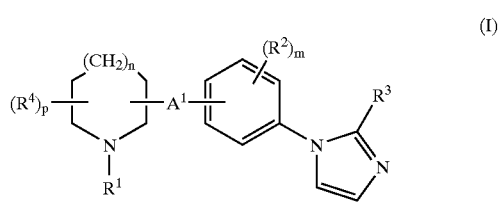

(I)

where m, n, p, $A^1$, $R^1$, $R^2$, $R^3$ and $R^4$ are described herein, as well as other N-heterocyclic derivatives, are useful as inhibitors of nitric oxide synthase. Pharmaceutical compositions containing these compounds, methods of using these compounds as inhibitors of nitric oxide synthase and processes for synthesizing these compounds are also described herein.

15 Claims, No Drawings

N-HETEROCYCLIC DERIVATIVES AS NOS INHIBITORS

This application claims the benefit of U.S. Provisional Application Ser. No. 60/377,274, filed Apr. 30, 2002, which is incorporated herein in full by reference.

FIELD OF THE INVENTION

The invention relates to a series of N-heterocyclic compounds and derivatives useful as inhibitors of nitric oxide synthase (NOS) and to methods of therapy for various diseases employing those compounds.

BACKGROUND OF THE INVENTION

Nitrogen monoxide (NO) has been implicated in a number of diverse physiological processes, including smooth muscle relaxation, platelet inhibition, nerve transmission, immune regulation and penile erection. Nitric oxide is produced under various conditions by virtually all nucleated mammalian cells. A number of pathologies are ascribed to abnormalities in NO production including stroke, insulin dependent diabetes, septic shock-induced hypotension, rheumatoid arthritis and multiple sclerosis. Nitric oxide is synthesized in biological tissues by an enzyme called nitric oxide synthase (NOS) which uses NADPH and molecular oxygen to oxidize L-arginine to citrulline and nitric oxide.

Nitric oxide synthase (NOS) exists in at least three isoforms, which fall into two primary categories: constitutive and inducible. Two constitutive isoforms, which are calcium and calmodulin dependent, have been identified, and one inducible isoform has been identified. The constitutive isoforms are (1) a neuronal isoform, NOS-1 or nNOS, which is found in the brain and skeletal muscles and (2) an endothelial isoform, NOS-3 or eNOS, which is expressed in the endothelium of blood vessels, the epithelium of the bronchial tree and in the brain. These constitutive isoforms are not the target of the NOS inhibitors of the present invention.

The inducible isoform (NOS2 or iNOS) is expressed in virtually all nucleated mammalian cells following exposure to inflammatory cytokines or lipopolysaccharide. Its presence in macrophages and lung epithelial cells is particularly noteworthy. The inducible isoform is neither stimulated by calcium nor blocked by calmodulin antagonists. It contains several tightly bound co-factors, including FMN, FAD and tetrahydrobiopterin.

Nitric oxide generated by the inducible form of NOS has been implicated in the pathogenesis of inflammatory diseases. In experimental animals, hypotension induced by lipopolysaccharide or tumor necrosis factor a can be reversed by NOS inhibitors. Conditions which lead to cytokine-induced hypotension include septic shock, hemodialysis and interleukin therapy in cancer patients. It is expected that an iNOS inhibitor would be effective in treating cytokine-induced hypotension. In addition, recent studies have suggested a role for NO in the pathogenesis of inflammation, and NOS inhibitors would therefore have beneficial effects on inflammatory bowel disease, cerebral ischemia and arthritis. Inhibitors of NOS may also be useful in treating acute respiratory distress syndrome (ARDS) and myocarditis, and they may be useful as adjuvants to short term immunosuppression in transplant therapy.

The diversity and ubiquity of NO function in physiology make the specific therapeutic targeting of NO-related phenomena an important consideration. Since endogenous NO production is the result of the actions of related but distinct isozymes, the differential inhibition of NOS isozymes allows more selective therapy with fewer side effects.

SUMMARY OF THE INVENTION

The compounds of the invention are inhibitors of iNOS and are therefore useful in conditions associated with the excessive production of iNOS. Accordingly, in one aspect, the invention is directed to compounds selected from the group consisting of the following formulae:

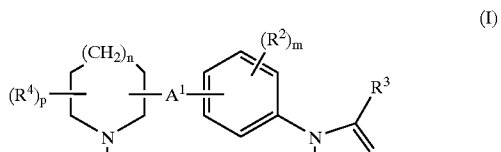

(I)

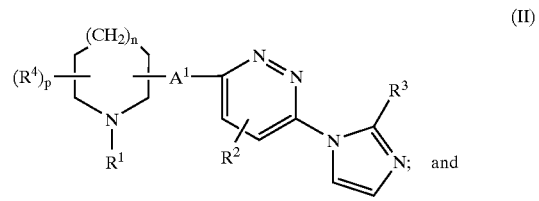

(II)

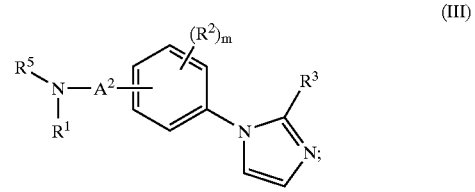

(III)

wherein:
each n is 0 to 2;
each m is 0 to 4;
each p is 0 to 2;
$A^1$ is —O—$(CH_2)_q$— (where q is 0 to 3), —$(CH_2)_q$—O— (where q is 0 to 3), —$N(R^6)$—$(CH_2)_q$— (where q is 0 to 3) or —$(CH_2)_q$—$N(R^6)$— (where q is 0 to 3);
$A^2$ is —$(CH_2)_q$—O— (where q is 2 to 3);
$R^1$ is hydrogen, alkyl, —$C(O)N(R^6)R^7$, or —$C(O)R^7$;
or $R^1$ is aralkyl (where the aryl radical is optionally substituted by one or more substituents selected from the group consisting of alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl, and dialkylaminocarbonyl);
or $R^1$ is heterocyclylalkyl (where the heterocyclyl radical is optionally substituted by one or more substituents selected from the group consisting of alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl, and dialkylaminocarbonyl);
each $R^2$ is independently halo, haloalkyl, alkyl, nitro, —$OR^6$, —$C(O)OR^6$, —$C(O)N(R^6)R^7$, —$N(R^6)R^7$, —$N(R^6)C(O)R^7$, or —$N(H)S(O)_2R^8$;
each $R^3$ is independently hydrogen or alkyl;
each $R^4$ is independently alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl, or dialkylaminocarbonyl;
$R^5$ is hydrogen, alkyl, aralkyl, —$(CH_2)_m$—$C(O)$—$OR^9$ (where m is 1 to 4), —$(CH_2)_m$—$C(O)$—$N(R^9)R^{10}$ (where m is 1 to 4), or heterocyclylalkyl (where the heterocyclyl radical is optionally substituted by one or more substituents selected from the group consisting of alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl, and dialkylaminocarbonyl);

each $R^6$ and $R^7$ is independently hydrogen, alkyl, aryl (optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl), aralkyl (wherein the aryl is optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl), heterocyclyl (optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl), or heterocyclylalkyl (wherein the heterocyclyl radical is optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl); and each $R^8$ is alkyl, aryl (optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl), or aralkyl (wherein the aryl is optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl);

each $R^9$ is independently hydrogen, alkyl or aralkyl (where the aryl radical is optionally substituted by one or more substituents selected from the group consisting of alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl, and dialkylaminocarbonyl); and $R^{10}$ is hydrogen, alkyl, or aralkyl (where the aryl radical is optionally substituted by one or more substituents selected from the group consisting of alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl, and dialkylaminocarbonyl);

or $R^{10}$ is heterocyclylalkyl (where the heterocyclyl radical is optionally substituted by one or more substituents selected from the group consisting of alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl, and dialkylaminocarbonyl);

as a single stereoisomer, a mixture of stereoisomers, or as a racemic mixture of stereoisomers; or a pharmaceutically acceptable salt thereof.

In another aspect, the invention is directed to pharmaceutical compositions useful in treating a condition in a mammal resulting from an abnormality in nitric oxide production, which compositions comprise a compound of the invention as described above and a pharmaceutically acceptable excipient.

In another aspect, the invention is directed to methods of treating a condition resulting from an abnormality in nitric oxide production which methods comprise administering to a mammal having a condition resulting from an abnormality in nitric oxide production a therapeutically effective amount of a compound of the invention as described above.

DETAILED DESCRIPTION OF THE INVENTION

Definitions

As used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, it is understood that for radicals, as defined below, that contain a substituted alkyl radical or that are attached to an alkyl radical, that the substitution or attachment can occur on any carbon of the alkyl radical.

"Alkoxy" refers to a radical of the formula —$OR_a$ where $R_a$ is an alkyl radical as defined above, e.g., methoxy, ethoxy, n-propoxy, 1-methylethoxy (iso-propoxy), n-butoxy, n-pentoxy, 1,1-dimethylethoxy (t-butoxy), and the like.

"Alkoxycarbonyl" refers to a radical of the formula —$C(O)OR_a$ where $R_a$ is an alkyl radical as defined above, e.g., methoxycarbonyl, ethoxycarbonyl, n-propoxycarbonyl, 1-methylethoxycarbonyl (iso-propoxycarbonyl), n-butoxycarbonyl, n-pentoxycarbonyl, 1,1-dimethylethoxycarbonyl (t-butoxycarbonyl), and the like.

"Amino" refers to the radical —$NH_2$.

"Aryl" refers to a phenyl or naphthyl radical. Unless stated otherwise specifically in the specification, the aryl radical may be optionally substituted by alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl, and dialkylaminocarbonyl.

"Aralkyl" refers to a radical of the formula —$R_aR_b$ where $R_a$ is an alkyl radical as defined above, substituted by $R_b$, an aryl radical, as defined above, e.g., benzyl. The aryl radical may be optionally substituted as described above.

"Aralkoxy" refers to a radical of the formula —$OR_c$ where $R_c$ is an aralkyl radical as defined above, e.g., benzyloxy, and the like. Unless stated otherwise specifically in the specification, the aryl radical in the aralkyl radical may be optionally substituted as described above.

"Aminocarbonyl" refers to the radical —$C(O)NH_2$.

"1,3-benzodioxol-5-yl" refers to the following radical:

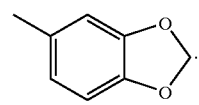

"(1,3-benzodioxol-5-yl)alkyl" refers to a radical of the formula —$R_a$—$R_c$ where $R_a$ is an alkyl radical as defined above and $R_c$ is a 1,3-benzodioxol-5-yl radical as defined above, e.g., 1-(1,3-benzodioxol-5-yl)methyl, 2-(1,3-benzodioxol-5-yl)ethyl, 3-(1,3-benzodioxol-5-yl)propyl, and the like.

"(1,3-benzodioxol-5-yl)carbonyl" refers to the radical of the formula —C(O)—$R_c$ where $R_c$ is a 1,3-benzodioxol-5-yl radical as defined above.

"Carboxy" refers to the radical —C(O)OH.

"Dialkylamino" refers to a radical of the formula —N($R_a$)$R_a$ where each $R_a$ is independently an alkyl radical as defined above, e.g., dimethylamino, methylethylamino, diethylamino, dipropylamino, ethylpropylamino, and the like.

"Dialkylaminocarbonyl" refers to a radical of the formula —C(O)N($R_a$)$R_a$ where each $R_a$ is independently an alkyl radical as defined above, e.g., dimethylaminocarbonyl, methylethylaminocarbonyl, diethylaminocarbonyl, dipropylaminocarbonyl, ethylpropylaminocarbonyl, and the like.

"Halo" refers to bromo, chloro, iodo or fluoro.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Heterocyclyl" refers to a stable 3- to 15-membered ring radical which consists of carbon atoms and from one to five heteroatoms selected from the group consisting of nitrogen, oxygen and sulfur. For purposes of this invention, the heterocyclyl radical may be a monocyclic, bicyclic or tricyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be aromatic or partially or fully saturated. The heterocyclyl radical may not be attached to the rest of the molecule at any heteroatom atom. Examples of such heterocyclyl radicals include, but are not limited to, azepinyl, acridinyl, benzimidazolyl, benzthiazolyl, benzoxazolyl, benzopyranyl, benzopyranonyl, benzofuranyl, benzofuranonyl, benzothienyl, benzodioxolanyl, benzodioxanyl, carbazolyl, cinnolinyl, decahydroisoquinolyl, dioxolanyl, furanyl, furanonyl, isothiazolyl, imidazolyl, imidazolinyl, imidazolidinyl, isothiazolidinyl, indolyl, isoindolyl, indolinyl, isoindolinyl, indolizinyl, isoxazolyl, isoxazolidinyl, morpholinyl, naphthyridinyl, oxadiazolyl, octahydroindolyl, octahydroisoindolyl, 2-oxopiperazinyl, 2-oxopiperidinyl, 2-oxopyrrolidinyl, 2-oxoazepinyl, oxazolyl, oxazolidinyl, oxiranyl, piperidinyl, piperazinyl, 4-piperidonyl, phenazinyl, phenothiazinyl, phenoxazinyl, phthalazinyl, pteridinyl, purinyl, pyrrolyl, pyrrolidinyl, pyrazolyl, pyrazolidinyl, pyridinyl, pyrazinyl, pyrimidinyl, pyridazinyl, quinazolinyl, quinoxalinyl, quinolinyl, quinuclidinyl, isoquinolinyl, thiazolyl, thiazolidinyl, thiadiazolyl, triazolyl, tetrazolyl, tetrahydrofuryl, triazinyl, tetrahydropyranyl, thienyl, thiamorpholinyl, thiamorpholinyl sulfoxide, and thiamorpholinyl sulfone. Unless stated otherwise specifically in the specification, the heteroalkyl radical may be optionally substituted by alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl, and dialkylaminocarbonyl.

"Heterocyclylalkyl" refers to a radical of the formula —$R_a$—$R_d$ where $R_a$ is an alkyl radical as defined above and $R_d$ is a heterocyclyl radical as defined above. The heterocyclyl radical may be optionally substituted as defined above.

"N-heterocyclylalkyl" refers to a heterocyclylalkyl radical as defined above wherein at least one of the heteroatoms is a nitrogen. The heterocyclyl radical of the N-heterocyclylalkyl radical may be optionally substituted by one or, more substituents selected from the group consisting of alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl, and dialkylaminocarbonyl.

"Mammal" includes humans and domesticated animals, such as cats, dogs, swine, cattle, sheep, goats, horses, rabbits, and the like.

"Monoalkylamino" refers to a radical of the formula —N(H)$R_a$ where $R_a$ is an alkyl radical as defined above, e.g., methylamino, ethylamino, propylamino, and the like.

"Monoalkylaminocarbonyl" refers to a radical of the formula —C(O)N(H)$R_a$ where $R_a$ is an alkyl radical as defined above, e.g., methylaminocarbonyl, ethylaminocarbonyl, propylaminocarbonyl, and the like.

"Nitro" refers to —$NO_2$.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7–9, 21–24 (Elsevier, Amsterdam).

A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Therapeutically effective amount" refers to that amount of a compound of the invention which, when administered to a mammal in need thereof, preferably a human, is sufficient to effect treatment, as defined below, for a condition resulting from an abnormality in nitric oxide production. The amount of a compound of the invention which constitutes a "therapeutically effective amount" will vary depending on the compound, the condition and its severity, and the age of the mammal, preferably a human, to be treated, but can be determined routinely by one of ordinary skill in the art having regard to his own knowledge and to this disclosure.

"Treating" or "treatment" as used herein covers the treatment of a condition in a mammal, preferably a human, which condition is characterized by an abnormality in nitric oxide production, and includes:

(i) preventing the condition from occurring in a mammal, in particular, when such mammal is predisposed to the condition but has not yet been diagnosed as having it;

(ii) inhibiting the condition, i.e., arresting its development; or (iii) relieving the condition, i.e., causing regression of the condition.

The yield of each of the reactions described herein is expressed as a percentage of the theoretical yield.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (R)- and (S)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The nomenclature used herein is a modified form of the I.U.P.A.C. nomenclature system wherein the compounds of the invention are named herein as derivatives of the central N-heterocyclic moiety. For example, the following compound of formula (I) wherein n is 1, m is 0, p is 0, $A^1$ is —O—, $R^1$ is 1,3-benzodioxol-5-ylmethyl, and $R^3$ is hydrogen, i.e.,

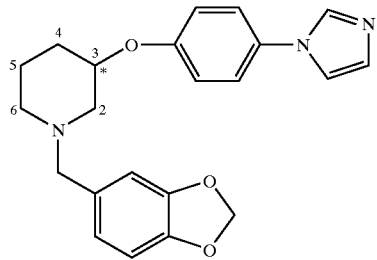

is named herein as 3-[4-(imidazol-1-yl)phenoxy]-1-[(1,3-benzodioxol-5-yl)methyl]piperidine. As noted above in the formula by the asterisk, the compound contains a chiral carbon at the 3-position of the piperidine. Unless otherwise indicated, compound names herein are intended to include any single stereoisomer, enantiomer, diastereomer, racemate or mixture of stereoisomers.

The use of parentheses in a formula herein is used to conserve space. Accordingly, the use of parenthesis in a formula indicates that the group enclosed within the parentheses is attached directly to the atom preceding the parenthesis. For example, the term —C(O)N($R^7$)$R^8$ can be drawn as follows:

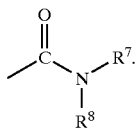

Utility of the Compounds of the Invention

Nitric oxide generated by the inducible form of nitric oxide synthase (iNOS) has been implicated in the pathogenesis of numerous inflammatory and autoimmune diseases and also in diseases which are generally not regarded as inflammatory, but nevertheless may involve cytokines which locally up-regulate i-NOS. The compounds of the invention, alone or in combination with other pharmaceutical agents, are therefore useful in treating mammals, preferably humans, having a condition resulting from an abnormality in nitric oxide production. Such conditions include, but are not limited to, the following:

Multiple sclerosis (Parkinson, J. F. et al., J. Mol. Med. (1997), Vol. 75, pp. 174–186); stroke or cerebral ischemia (Iadecola, C. et al., J. Neurosci. (1997), Vol. 17, pp. 9157–9164); Alzheimer's disease (Smith, M. A. et al., J. Neurosci. (1997), Vol. 17, pp. 2653–2657; Wallace, M. N. et al., Exp. Neurol. (1997), Vol. 144, pp. 266–272); HIV dementia (Adamson D. C. et al., Science (1996), Vol. 274, pp. 1917–1921); Parkinson's disease (Hunot, S. et al., Neuroscience (1996), Vol. 72, pp. 355–363); meningitis (Koedel, U. et al., Ann. Neurol. (1995), Vol. 37, pp. 313–323); dilated cardiomyopathy and congestive heart failure (Satoh M et al., J. Am. Coll. Cardiol. (1997), Vol. 29, pp. 716–724); atherosclerosis (Wilcox, J. N. et al., Arterioscler. Thromb. Vasc. Biol. (1997), Vol. 17, pp. 2479–2488); restenosis or graft stenosis, septic shock and hypotension (Petros, A. et al., Cardiovasc. Res. (1994), Vol. 28, pp. 34–39); hemorrhagic shock (Thiemermann, C. et al., Proc. Natl. Acad. Sci. (1993), Vol. 90, pp. 267–271); asthma (Barnes, P. J., Ann. Med. (1995), Vol. 27, pp. 389–393; Flak, T. A. et al., Am. J. Respir. Crit. Care Med. (1996), Vol. 154, pp. S202-S206); acute respiratory distress syndrome, smoke or particulate-mediated lung injury (Ischiropoulos, H. et al., Am. J. Respir. Crit. Care Med. (1994), Vol. 150, pp. 337–341; Van Dyke, K., Agents Actions (1994), Vol. 41, pp. 44–49); pathogen-mediated pneumonias (Adler, H. et al., J. Exp. Med. (1997), Vol. 185, pp. 1533–1540); trauma of various etiologies (Thomae, K. R. et al., Surgery (1996), Vol. 119, pp. 61–66); rheumatoid arthritis and osteoarthritis (Grabowski, P. S. et al., Br. J. Rheumatol. (1997), Vol. 36, pp. 651–655); glomerulonephritis (Weinberg, J. B. et al., J. Exp. Med. (1994), Vol. 179, pp. 651–660); systemic lupus erythematosus (Belmont, H. M. et al., Arthritis Rheum. (1997), Vol. 40, pp. 1810–1816); inflammatory bowel diseases such as ulcerative colitis and Crohn's disease (Godkin, A. J. et al., Eur. J. Clin. Invest. (1996), Vol. 26, pp. 867–872; Singer, I. I. et al., Gastroenterology (1996), Vol. 111, pp. 871–885); insulin dependent diabetes mellitus (McDaniel, M. L., et al., Proc. Soc. Exp. Biol. Med. (1996), Vol. 211, pp. 24–32); diabetic neuropathy or nephropathy (Sugimoto, K. and Yagihashi, S., Microvasc. Res. (1997), Vol. 53, pp. 105–112; Amore, A. et al., Kidney Int. (1997), Vol. 51, pp. 27–35); acute and chronic organ transplant rejection (Worrall, N. K. et al., Transplantation (1997), Vol. 63, pp. 1095–1101); transplant vasculopathies (Russell, M. E. et al., (1995), Vol. 92, pp. 457–464); graft-versus-host disease (Kichian, K. et al., J. Immunol. (1996), Vol. 157, pp. 2851–2856); psoriasis and other inflammatory skin diseases (Bruch-Gerharz, D. et al., J. Exp. Med. (1996), Vol. 184, pp. 2007–2012); and cancer (Thomsen, L. L. et al., Cancer Res. (1997), Vol. 57, pp. 3300–3304).

The compounds of the current invention may also be useful for the management of male and female reproductive functions when used alone or combined with other drugs commonly used for these indications. Examples, without implied limitation, include: inhibition of fertilization, endometrial receptivity and implantation (alone or in combination with a progesterone antagonist); post-coital contraception (alone or in combination with a progesterone antagonist); induction of abortion (in combination with an antiprogestin and in further combination with a prostaglandin); control and management of labor and delivery; treatment of cervical incompetence (alone or in combination with progesterone or a progestin); treatment of endometriosis (alone or in combination with other drugs, including LHRH-agonists/antagonists, antiprogestins or progestins by either sequential application or by concomitant administration). See, for example, the following references: Chwalisz, K. et al., J. Soc. Gynecol. Invest. (1997), Vol. 4, No. 1 (Supplement), page 104a, which discusses the inhibition of fertilization, endometrial receptivity and implantation, or post-coital contraception, alone or in combination with a progesterone antagonist; Chwalisz, K. et al., Prenat. Neonat. Med. (1996), Vol. 1, pp. 292–329, which discusses the induction of abortion, in combination with an antiprogestin and in further combination with a prostaglandin, and the control and management of labor and delivery; and Chwalisz, K. et al., Hum. Reprod. (1997), vol.12, pp. 101–109, which discusses the treatment of cervical incompetence, alone or in combination with progesterone or a progestin.

Those skilled in the art will also recognize that the compounds of the present invention include 1-substituted imidazoles. This class of compounds has previously been described as mechanism-based, heme-binding inhibitors of the cytochrome P450 family of enzymes (Maurice, M. et al., *FASEB J.* (1992), Vol. 6, pp. 752–8) in addition to nitric oxide synthesis (Chabin, R. N M. et al., *Biochemistry* (1996), Vol. 35, pp. 9567–9575). The compounds of the present invention may thus be useful as inhibitors of selected cytochrome P450 family members of therapeutic interest including, but not limited to, P450 enzymes involved in steroid and retinoid biosynthesis (Masamura et al., *Breast Cancer Res. Treat.* (1995), Vol. 33, pp. 19–26; Swart, P. et al., *J. Clin. Endocrinol. Metab.*, Vol. 77, pp. 98–102; Docks, P. et al., *Br. J. Dermatol.* (1995), Vol. 133, pp. 426–32) and cholesterol biosynthesis (Burton, P. M. et al., *Biochem. Pharmacol.* (1995), Vol. 50, pp. 529–544; and Swinney, D. C. et al., *Biochemistry* (1994), Vol. 33, pp. 4702–4713). Imidazole-based compounds may also have antifungal activity (Aoyama, Y. et al., *Biochem. Pharmacol.* (1992), Vol. 44, pp. 1701–1705).

Testing of the Compounds of the Invention

Nitric oxide synthases are complex enzymes that catalyze the conversion of L-arginine to nitric oxide (NO) and citrulline. Catalysis proceeds through two successive oxidations of the guanidinium group of L-arginine.

A cell-based nitric oxide synthase assay employing the measurement of nitric oxide oxidation product, nitrite, in the conditioned medium of cultured cells was employed for the evaluation of the compounds of the invention in vitro. The murine monocytic cell lines RAW 264.7 and J774 are well documented as capable of producing >10:M nitrite in response to immunostimulation. This in vitro assay is described in detailed below in the Examples.

Various in vivo assays may be employed to determine the efficacy of the compounds of the invention in treating a condition resulting from an abnormality in nitric oxide production, such as arthritis. Such an assay is described in detail below in the Examples.

Those skilled in the art will also recognize that numerous assays for the activity of the NOS isoforms (iNOS, nNOS and eNOS) exist which can be used to evaluate the biological activity of the compounds of the current invention. These include assays for native NOS isoforms in tissues studied ex vivo (Mitchell et al., *Br. J. Pharmacol.* (1991), Vol. 104, pp. 289–291; Szabo et al., *Br. J. Pharmacol.* (1993), Vol. 108, pp. 786–792; Joly et al., *Br. J. Pharmacol.* (1995), Vol. 115, pp. 491–497) as well as primary cell cultures and cell lines (Forstermann et al., *Eur. J. Pharmacol.* (1992), Vol. 225, pp. 161–165; Radmoski et al., *Cardiovasc. Res.* (1993), Vol. 27, pp. 1380–1382; Wang et al., *J. Pharmacol. Exp. Ther.* (1994), Vol. 268, pp. 552–557). Those skilled in the art will also recognize that recombinant NOS enzymes can be expressed in heterologous cells by either transient transfection (Karlsen et al., *Diabetes,* (1995), Vol. 44, pp. 753–758), stable transfection (McMillan et al., *Proc. Natl. Acad. Sci.* (1992), Vol. 89, pp. 11141–11145; Sessa et al., *J. Biol. Chem.* (1995), Vol. 270, pp. 17641–17644) or via the use of lytic virus transfection (Busconi & Michel, *Mol. Pharmacol.* (1995), Vol. 47, pp. 655–659; List et al., *Biochem. J.* (1996), Vol. 315, pp. 57–63) using NOS cDNAs. Heterologous expression can be achieved in mammalian cells (McMillan et al., *Proc. Natl. Acad. Sci.* (1992), Vol. 89, pp. 11141–11145), insect cells (Busconi & Michel, *Mol. Pharmacol.* (1995), Vol. 47, pp. 655–659; List et al., *Biochem. J.* (1996), Vol. 315, pp. 57–63), yeast (Sari et al., *Biochemistry* (1996), Vol. 35, pp. 7204–7213) or bacteria (Roman et al., *Proc. Natl. Acad. Sci.* (1995), Vol. 92, pp. 8428–8432; Martasek et al., *Biochem. Biophys. Res. Commun.* (1996), Vol. 219, pp. 359–365). Any of these heterologous expression systems can be used to establish iNOS, nNOS and eNOS assay systems to evaluate the biological activity of the compounds of the present invention.

The P450 inhibitory activity of the compounds of the present invention can be assessed using appropriate assay systems specific for the P450 isoform of interest. Such assays are included in the references cited in the discussion of P450 family of enzymes in Paragraph B above. One additional example of mammalian cytochrome P450 isoform that may be inhibited by the compounds of the present invention is cytochrome P450 3A4 which can be assayed in a manner similar to the method described in Yamazaki et al., *Carcinogenesis* (1995), Vol. 16, pp. 2167–2170.

Administration of the Compounds of the Invention

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the present invention may be in any form that allows for the composition to be administered to a patient. Typical routes of administration include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state characterized by inflammation in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, e.g., inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, e.g., a gelatin capsule, it may contain, in addition to materials of the above type, a liquid carrier such as polyethylene glycol or a fatty oil.

The pharmaceutical composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 1% by weight of the compound of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, e.g., of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units which can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

Whether in solid, liquid or gaseous form, the pharmaceutical composition of the present invention may contain one or more known pharmacological agents used in the treatment of inflammation.

The pharmaceutical compositions of the invention may be prepared by methodology well known in the pharmaceutical art. For example, a pharmaceutical composition intended to be administered by injection can be prepared by combining a compound of the invention with water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disease-state; and the host undergoing therapy. Generally, a therapeutically effective daily dose is from about 0.14 mg to about 14.3 mg/kg of body weight per day of a compound of the invention, or a pharmaceutically acceptable salt thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of a compound of the invention, or a pharmaceutically acceptable salt thereof, preferably from about 50 mg to about 700 mg per day, and most preferably from about 100 mg to about 500 mg per day.

PREFERRED EMBODIMENTS

Of the compounds of the invention as described above in the Summary of the Invention, certain groups of compounds are particularly preferred.

Accordingly, one preferred group is that group of compounds wherein the compound is selected from formula (I):

(I)

$(R^4)_p$—[ring with $(CH_2)_n$]—$A^1$—[phenyl with $(R^2)_m$]—N—[imidazole with $R^3$]
         |
         N
         |
         $R^1$ Of this preferred group of compounds, a preferred subgroup is that subgroup of compounds wherein:
n, m and p are each independently 0 to 2;
$A^1$ is —O—$(CH_2)_q$— (where q is 0 to 1), —$(CH_2)_q$—O— (where q is 0 to 1), —$N(R^6)$—$(CH_2)_q$— (where q is 0 to 1) or —$(CH_2)_q$—$N(R^6)$— (where q is 0 to 1);
$R^1$ is aralkyl (where the aryl radical is optionally substituted by one or more substituents selected from the group consisting of alkyl, halo, haloalkyl, hydroxy, alkoxy, amino, dialkylamino, monoalkylamino, nitro, carboxy, alkoxycarbonyl, aminocarbonyl, monoalkylaminocarbonyl, and dialkylaminocarbonyl);
or $R^1$ is (1,3-benzodioxol-5-yl)alkyl (where the benzodioxolyl radical is optionally substituted by one or more substituents selected from the group consisting of alkyl, halo, haloalkyl, hydroxy, alkoxy, amino, dialkylamino, monoalkylamino, nitro, carboxy, alkoxycarbonyl, aminocarbonyl, monoalkylaminocarbonyl, and dialkylaminocarbonyl);
or $R^1$ is (1,3-benzodioxol-5-yl)carbonyl (where the benzodioxolyl radical is optionally substituted by one or more substituents selected from the group consisting of alkyl, halo, haloalkyl, hydroxy, alkoxy, amino, dialkylamino, monoalkylamino, nitro, carboxy, alkoxycarbonyl, aminocarbonyl, monoalkylaminocarbonyl, and dialkylaminocarbonyl);
$R^2$ is halo, haloalkyl, alkyl, nitro, —$OR^6$, —$C(O)OR^6$, —$C(O)N(R^6)R^7$, or —$N(R^6)R^7$;
each $R^3$ is independently hydrogen or alkyl;
each $R^4$ is independently alkyl, halo, haloalkyl, hydroxy, alkoxy, amino, dialkylamino, monoalkylamino, nitro, carboxy, alkoxycarbonyl, aminocarbonyl, monoalkylaminocarbonyl, or dialkylaminocarbonyl; and
each $R^6$ and $R^7$ is independently hydrogen or alkyl.

Of this preferred subgroup of compounds, a preferred class is that class of compounds wherein:
n, m and p are each independently 0 to 2;
$A^1$ is —O—, —$CH_2$—O—, or —$N(R^6)$—;
$R^1$ is aralkyl (where the aryl radical is optionally substituted by one or more substituents selected from the group consisting of alkyl, hydroxy, and alkoxy);
or $R^1$ is (1,3-benzodioxol-5-yl)alkyl (where the benzodioxolyl radical is optionally substituted by one or more substituents selected from the group consisting of alkyl, hydroxy, and alkoxy);
or $R^1$ is (1,3-benzodioxol-5-yl)carbonyl (where the benzodioxolyl radical is optionally substituted by one or more substituents selected from the group consisting of alkyl, hydroxy, and alkoxy);
$R^2$ is halo, haloalkyl, alkyl, or —$OR^6$;
each $R^3$ is independently hydrogen or alkyl;
each $R^4$ is independently alkyl, halo, haloalkyl, hydroxy, alkoxy, amino, dialkylamino, monoalkylamino, nitro, carboxy, alkoxycarbonyl, aminocarbonyl, monoalkylaminocarbonyl, or dialkylaminocarbonyl; and
$R^6$ is hydrogen or alkyl.

Of this preferred class of compounds, a preferred subclass is that subclass of compounds wherein:
n is 0 to 2;
m is 0 to 1;
p is 0 to 2;
$A^1$ is —O—, —$CH_2O$— or —$N(R^6)$—;
$R^1$ is aralkyl (where the aryl radical is optionally substituted by one or more substituents selected from the group consisting of alkyl, hydroxy, and alkoxy);
or $R^1$ is (1,3-benzodioxol-5-yl)alkyl (where the benzodioxolyl radical is optionally substituted by one or more substituents selected from the group consisting of alkyl, hydroxy, and alkoxy);
or $R^1$ is (1,3-benzodioxol-5-yl)carbonyl (where the benzodioxolyl radical is optionally substituted by one or more substituents selected from the group consisting of alkyl, hydroxy, and alkoxy);
$R^2$ is halo, haloalkyl, alkyl, or —$OR^6$;
each $R^3$ is hydrogen or alkyl;
each $R^4$ is independently alkyl, halo, haloalkyl, hydroxy, alkoxy, amino, dialkylamino, monoalkylamino, nitro, carboxy, alkoxycarbonyl, aminocarbonyl, monoalkylaminocarbonyl, or dialkylaminocarbonyl; and
$R^6$ is hydrogen or alkyl.

Of this preferred subclass of compounds, a preferred set is that set of compounds wherein:
n is 0;
m is 0 to 1;
p is 0 to 2;
$A^1$ is —O—;
$R^1$ is aralkyl (where the aryl radical is optionally substituted by one or more substituents selected from the group consisting of alkyl, hydroxy, and alkoxy);
$R^2$ is halo, haloalkyl, alkyl, or —$OR^6$;
$R^3$ is hydrogen or alkyl;
each $R^4$ is independently alkyl, halo, haloalkyl, hydroxy, alkoxy, amino, dialkylamino, monoalkylamino, nitro, carboxy, alkoxycarbonyl, aminocarbonyl, monoalkylaminocarbonyl, or dialkylaminocarbonyl; and
$R^6$ is hydrogen or alkyl.

Another preferred set of compounds of this subclass of compounds is that set of compounds wherein:
n is 0;
m is 0 to 1;
p is 0 to 2;
$A^1$ is —O— or —$CH_2O$—;
$R^1$ is (1,3-benzodioxol-5-yl)alkyl (where the benzodioxolyl radical is optionally substituted by one or more substituents selected from the group consisting of alkyl, hydroxy, and alkoxy);
$R^2$ is halo, haloalkyl, alkyl, or —$OR^6$;
$R^3$ is hydrogen or alkyl;
each $R^4$ is independently alkyl, halo, haloalkyl, hydroxy, alkoxy, amino, dialkylamino, monoalkylamino, nitro, carboxy, alkoxycarbonyl, aminocarbonyl, monoalkylaminocarbonyl, or dialkylaminocarbonyl; and
$R^6$ is hydrogen or alkyl.

Of this preferred set of compounds, preferred compounds are selected from the group consisting of the following compounds:

3-[4-(imidazol-1-yl)phenoxy]-1-[(1,3-benzodioxol-5-yl)methyl]pyrrolidine;
(3S)-3-[4-(imidazol-1-yl)phenoxy]-1-[(1,3-benzodioxol-5-yl)methyl]pyrrolidine;
(3R)-3-[4-(imidazol-1-yl)phenoxy]-1-[(1,3-benzodioxol-5-yl)methyl]pyrrolidine;
2-methoxycarbonyl-4-[4-(imidazol-1-yl)phenoxy]-1-[(1,3-benzodioxol-5-yl)methyl]pyrrolidine
2-carboxy-4-[4-(imidazol-1-yl)phenoxy]-1-[(1,3-benzodioxol-5-yl)methyl]pyrrolidine; and
2-[(4-(imidazol-1-yl)phenoxy)methyl]-1-[(1,3-benzodioxol-5-yl)methyl]pyrrolidine.

Another preferred set of compounds of this subclass of compounds is that set of compounds wherein:
n is 0;
m is 0 to 1;
p is 0 to 2;
$A^1$ is —O—;
$R^1$ is (1,3-benzodioxol-5-yl)carbonyl (where the benzodioxolyl radical is optionally substituted by one or more substituents selected from the group consisting of alkyl, hydroxy, and alkoxy);
$R^2$ is halo, haloalkyl, alkyl, or —$OR^6$;
$R^3$ is hydrogen or alkyl;
each $R^4$ is independently alkyl, halo, haloalkyl, hydroxy, alkoxy, amino, dialkylamino, monoalkylamino, nitro, carboxy, alkoxycarbonyl, aminocarbonyl, monoalkylaminocarbonyl, or dialkylaminocarbonyl; and
$R^6$ is hydrogen or alkyl.

Of this preferred set of compounds, a preferred compounds is 3-[4-(imidazol-1-yl)phenoxy]-1-[(1,3-benzodioxol-5-yl)carbonyl]pyrrolidine.

Another preferred set of compounds of this subclass of compounds is that set of compounds wherein:
n is 1 or 2;
m is 0 to 1;
p is 0 to 2;
$A^1$ is —O—, —$CH_2$—O— or —N(H)—;
$R^1$ is aralkyl (where the aryl radical is optionally substituted by one or more substituents selected from the group consisting of alkyl, hydroxy, and alkoxy);
or $R^1$ is (1,3-benzodioxol-5-yl)alkyl (where the benzodioxolyl radical is optionally substituted by one or more substituents selected from the group consisting of alkyl, hydroxy, and alkoxy);
$R^2$ is halo, haloalkyl, alkyl, or —$OR^6$;
$R^3$ is hydrogen or alkyl;
each $R^4$ is independently alkyl, halo, haloalkyl, hydroxy, alkoxy, amino, dialkylamino, monoalkylamino, nitro, carboxy, alkoxycarbonyl, aminocarbonyl, monoalkylaminocarbonyl, or dialkylaminocarbonyl; and
$R^6$ is hydrogen or alkyl.

Of this preferred set of compounds, a preferred subset is that subset of compounds wherein:
$A^1$ is —O—, —$CH_2$O— or —N(H)—; and
$R^1$ is (1,3-benzodioxol-5-yl)alkyl (where the benzodioxolyl radical is optionally substituted by one or more substituents selected from the group consisting of alkyl, hydroxy, and alkoxy).

Of this preferred subset of compounds, preferred compounds are selected from the group consisting of the following compounds:
3-[4-(imidazol-1-yl)phenoxy]-1-[(1,3-benzodioxol-5-yl)methyl]piperidine;
(3S)-3-[4-(imidazol-1-yl)phenoxy]-1-[(1,3-benzodioxol-5-yl)methyl]piperidine;
(3R)-3-[4-(imidazol-1-yl)phenoxy]-1-[(1,3-benzodioxol-5-yl)methyl]piperidine;
2-[(4-(imidazol-1-yl)phenoxy)methyl]-1-[(1,3-benzodioxol-5-yl)methyl]piperidine;
3-[(4-(imidazol-1-yl)phenoxy)methyl]-1-[(1,3-benzodioxol-5-yl)methyl]piperidine;
3-[(4-(imidazol-1-yl)phenyl)amino]-1-[(1,3-benzodioxol-5-yl)methyl]piperidine; and
3-[4-(imidazol-1-yl)phenoxy]-1-[(1,3-benzodioxol-5-yl)methyl]hexahydro-1H-azepine.

Another preferred subset of compounds of this set of compounds is that subset of compounds wherein:
$A^1$ is —O—; and
$R^1$ is aralkyl (where the aryl radical is optionally substituted by one or more substituents selected from the group consisting of alkyl, hydroxy, and alkoxy).

Of this preferred subset of compounds, preferred compounds are selected from the group consisting of the following compounds:
3-[4-(imidazol-1-yl)phenoxy]-1-(3,4-dimethoxybenzyl)piperidine; and
3-[4-(imidazol-1-yl)phenoxy]-1-(4-methoxynaphth-1-yl)methylpiperidine.

Another preferred group of compounds of the invention as set forth above in the Summary of the Invention is that group of compounds selected from formula (II):

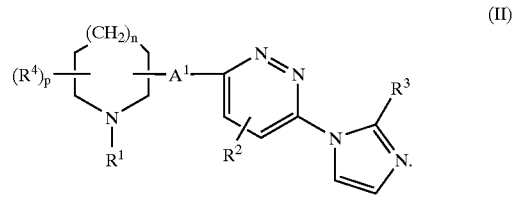

(II)

Of this preferred group of compounds, a preferred subgroup is that subgroup of compounds wherein:
n and p are each independently 0 to 2;
$A^1$ is —O—$(CH_2)_q$— (where q is 0 to 1), —$(CH_2)_q$—O— (where q is 0 to 1), —$N(R^6)$—$(CH_2)_q$— (where q is 0 to 1); or —$(CH_2)_q$—$N(R^6)$— (where q is 0 to 1);
$R^1$ is (1,3-benzodioxol-5-yl)alkyl (where the benzodioxolyl radical is optionally substituted by one or more substituents selected from the group consisting of alkyl, halo, haloalkyl, hydroxy, alkoxy, amino, dialkylamino, monoalkylamino, nitro, carboxy, alkoxycarbonyl, aminocarbonyl, monoalkylaminocarbonyl, and dialkylaminocarbonyl);
$R^2$ is halo, haloalkyl, alkyl, nitro, —$OR^6$, —$C(O)OR^6$, —$C(O)N(R^6)R^7$, or —$N(R^6)R^7$;
each $R^3$ is independently hydrogen or alkyl;
each $R^4$ is independently alkyl, halo, haloalkyl, hydroxy, alkoxy, amino, dialkylamino, monoalkylamino, nitro, carboxy, alkoxycarbonyl, aminocarbonyl, monoalkylaminocarbonyl, or dialkylaminocarbonyl; and
each $R^6$ and $R^7$ is independently hydrogen or alkyl.

Of this preferred subgroup of compounds, a preferred class is that class of compounds wherein:
n and p are each independently 0 to 2;
$A^1$ is —O—, —$CH_2$—O—, or —$N(R^6)$—;
$R^1$ is (1,3-benzodioxol-5-yl)alkyl (where the benzodioxolyl radical is optionally substituted by one or more substituents selected from the group consisting of alkyl, hydroxy, and alkoxy);
$R^2$ is halo, haloalkyl, alkyl, or —$OR^6$;
each $R^3$ is independently hydrogen or alkyl;
each $R^4$ is independently alkyl, halo, haloalkyl, hydroxy, alkoxy, amino, dialkylamino, monoalkylamino, nitro, carboxy, alkoxycarbonyl, aminocarbonyl, monoalkylaminocarbonyl, or dialkylaminocarbonyl; and $R^6$ is hydrogen or alkyl.

Of this preferred class of compounds, a preferred subclass is that subclass of compounds wherein:
n is 0 to 2;
p is 0 to 2;
$A^1$ is —O— or —CH$_2$O—;
$R^1$ is (1,3-benzodioxol-5-yl)alkyl (where the benzodioxolyl radical is optionally substituted by one or more substituents selected from the group consisting of alkyl, hydroxy, and alkoxy);
$R^2$ is halo, haloalkyl, alkyl, or —OR$^6$;
$R^3$ is hydrogen or alkyl;
each $R^4$ is independently alkyl, halo, haloalkyl, hydroxy, alkoxy, amino, dialkylamino, monoalkylamino, nitro, carboxy, alkoxycarbonyl, aminocarbonyl, monoalkylaminocarbonyl, or dialkylaminocarbonyl; and
$R^6$ is hydrogen or alkyl.

Of this preferred subclass of compounds, preferred compounds are selected from the group consisting of the following compounds:
3-[(6-(imidazol-1-yl)pyridazin-3-yl)oxy]-1-[(1,3-benzodioxol-5-yl)methyl]piperidine; and
2-[((6-(imidazol-1-yl)pyridazin-3-yl)oxy)methyl]-1-[(1,3-benzodioxol-5-yl)methyl]piperidin.

Another preferred group of compounds of the invention as set forth above in the Summary of the Invention is that group of compounds selected from formula (III):

(III)

Of this preferred group of compounds, a preferred subgroup is that subgroup of compounds wherein:
m is 0 to 4;
$A^2$ is —(CH$_2$)$_q$—O— (where q is 2 to 3);
$R^1$ is aralkyl (where the aryl radical is optionally substituted by one or more substituents selected from the group consisting of alkyl, halo, haloalkyl, hydroxy, alkoxy, amino, dialkylamino, monoalkylamino, nitro, carboxy, alkoxycarbonyl, aminocarbonyl, monoalkylaminocarbonyl, and dialkylaminocarbonyl);
or $R^1$ is (1,3-benzodioxol-5-yl)alkyl (where the benzodioxolyl radical is optionally substituted by one or more substituents selected from the group consisting of alkyl, halo, haloalkyl, hydroxy, alkoxy, amino, dialkylamino, monoalkylamino, nitro, carboxy, alkoxycarbonyl, aminocarbonyl, monoalkylaminocarbonyl, and dialkylaminocarbonyl);
each $R^2$ is independently halo, haloalkyl, alkyl, —OR$^6$, —C(O)OR$^6$, —C(O)N(R$^6$)R$^7$, —N(R$^6$)R$^7$, or —N(R$^6$)C(O)R$^7$;
$R^3$ is independently hydrogen or alkyl;
$R^5$ is hydrogen, alkyl, aralkyl, —(CH$_2$)$_m$—C(O)—OR$^9$ (where m is 1 to 4), —(CH$_2$)$_m$—C(O)—N(R$^9$)R$^{10}$ (where m is 1 to 4), or (1,3-benzodioxol-5-yl)alkyl (where the benzodioxolyl radical is optionally substituted by one or more substituents selected from the group consisting of alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl, and dialkylaminocarbonyl);
each $R^6$ and $R^7$ is independently hydrogen or alkyl;
each $R^9$ is independently hydrogen or alkyl; and
$R^{10}$ is hydrogen, alkyl, aralkyl (where the aryl radical is optionally substituted by one or more substituents selected from the group consisting of alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl, and dialkylaminocarbonyl);
or $R^{10}$ is (1,3-benzodioxol-5-yl)alkyl (where the benzodioxolyl radical is optionally substituted by one or more substituents selected from the group consisting of alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl, and dialkylaminocarbonyl);
or $R^{10}$ is N-heterocyclylalkyl (where the heterocyclyl radical is optionally substituted by one or more substituents selected from the group consisting of alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl, and dialkylaminocarbonyl).

Of this subgroup of compounds, a preferred class is that class of compounds wherein:
m is 0;
$A^2$ is —CH$_2$—CH$_2$—O—;
$R^1$ is (1,3-benzodioxol-5-yl)alkyl (where the benzodioxolyl radical is optionally substituted by one or more substituents selected from the group consisting of alkyl, halo, haloalkyl, hydroxy, alkoxy, amino, dialkylamino, monoalkylamino, nitro, carboxy, alkoxycarbonyl, aminocarbonyl, monoalkylaminocarbonyl, and dialkylaminocarbonyl);
$R^3$ is hydrogen;
$R^5$ is hydrogen, —(CH$_2$)$_m$—C(O)—OR$^9$ (where m is 1 to 4), —(CH$_2$)$_m$—C(O)—N(R$^9$)R$^{10}$ (where m is 1 to 4), or (1,3-benzodioxol-5-yl)alkyl;
each $R^9$ is independently hydrogen or alkyl; and
$R^{10}$ is hydrogen, alkyl, aralkyl (where the aryl radical is optionally substituted by one or more substituents selected from the group consisting of alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl, and dialkylaminocarbonyl);
or $R^{10}$ is (1,3-benzodioxol-5-yl)alkyl (where the benzodioxolyl radical is optionally substituted by one or more substituents selected from the group consisting of alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl, and dialkylaminocarbonyl);
or $R^{10}$ is N-heterocyclylalkyl (where the heterocyclyl radical is optionally substituted by by one or more substituents selected from the group consisting of alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl, and dialkylaminocarbonyl).

Of this preferred class of compounds, a preferred subclass is that subclass of compounds wherein:
$R^1$ is (1,3-benzodioxol-5-yl)methyl;
$R^5$ is hydrogen, —CH$_2$—C(O)—OR$^9$, —CH$_2$—C(O)—N(R$^9$)R$^{10}$, or (1,3-benzodioxol-5-yl)methyl;
each $R^9$ is independently hydrogen or alkyl; and
$R^{10}$ is hydrogen, alkyl, aralkyl (where the aryl radical is optionally substituted by one or more substituents selected from the group consisting of alkyl, halo, haloalkyl, hydroxy, alkoxy, amino, dialkylamino, monoalkylamino, carboxy, alkoxycarbonyl, aminocarbonyl, monoalkylaminocarbonyl, and dialkylaminocarbonyl);

or $R^{10}$ is (1,3-benzodioxol-5-yl)methyl; and or $R^{10}$ is piperidin-1-ylalkyl (wherein the piperidinyl radical is optionally substituted by one or more substituents selected from the group consisting of alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl, and dialkylaminocarbonyl).

Of this preferred subclass of compounds, a preferred set is that set of compounds wherein:

$R^5$ is hydrogen or —$CH_2$—C(O)—$OR^9$; and $R^9$ is hydrogen or alkyl.

Of this preferred set of compounds, preferred compounds are selected from the group consisting of the following compounds:

N-[2-(4-(imidazol-1-yl)phenoxy)ethyl]-N-[(1,3-benzodioxol-5-yl)methyl]amine;

N-(carboxymethyl)-N-[2-(4-(imidazol-1-yl)phenoxy)ethyl]-N-[(1,3-benzodioxol-5-yl)methyl]amine; and N-(ethoxycarbonylmethyl)-N-[2-(4-(imidazol-1-yl)phenoxy)ethyl]-N-[(1,3-benzodioxol-5-yl)methyl]amine.

Another preferred set of compound of this preferred subclass of compounds is that set of compounds wherein $R^5$ is (1,3-benzodioxol-5-yl)methyl, namely, N-[2-(4-(imidazol-1-yl)phenoxy)ethyl]-N,N-di[(1,3-benzodioxol-5-yl)methyl]amine.

Another preferred set of compounds of this preferred subclass of compounds is that set of compounds wherein:

$R^5$ is —$CH_2$—C(O)—$N(R^9)R^{10}$;

$R^9$ is independently hydrogen or alkyl; and $R^{10}$ is hydrogen, alkyl, aralkyl (where the aryl radical is optionally substituted by one or more substituents selected from the group consisting of alkyl, halo, haloalkyl, hydroxy, alkoxy, amino, dialkylamino, monoalkylamino, carboxy, alkoxycarbonyl, aminocarbonyl, monoalkylaminocarbonyl, and dialkylaminocarbonyl);

or $R^{10}$ is (1,3-benzodioxol-5-yl)methyl; and or $R^{10}$ is piperidin-1-ylalkyl (wherein the piperidinyl radical is optionally substituted by one or more substituents selected from the group consisting of alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl, and dialkylaminocarbonyl).

Of this preferred set of compounds, preferred compounds are selected from the group consisting of the following compounds:

N-[(((3-(2-methylpiperidin-1-yl)propyl)amino)carbonyl)methyl]-N-[2-(4-(imidazol-1-yl)phenoxy)ethyl]-N-[(1,3-benzodioxol-5-yl)methyl]amine;

N-[((((1,3-benzodioxol-5-yl)methyl)amino)carbonyl)methyl]-N-[2-(4-(imidazol-1-yl)phenoxy)ethyl]-N-[(1,3-benzodioxol-5-yl)methyl]amine;

N-[((((4-trifluoromethylphenyl)methyl)amino)carbonyl)methyl]-N-[2-(4-(imidazol-1-yl)phenoxy)ethyl]-N-[(1,3-benzodioxol-5-yl)methyl]amine; and N-[(((butyl)amino)carbonyl)methyl]-N-[2-(4-(imidazol-1-yl)phenoxy)ethyl]-N-[(1,3-benzodioxol-5-yl)methyl]amine.

Preparation of the Compounds of the Invention

It is understood that in the following description, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, amino, mercapto and carboxylic acid. Suitable protecting groups for hydroxy include trialkylsilyl or diaryllalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—$R^8$ (where $R^8$ is alkyl, alkenyl, aryl, aralkyl or aralkenyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein.

The use of protecting groups is described in detail in Green, T. W. and P. G. M. Wutz, *Protective Groups in Organic Synthesis* (1991), 2nd Ed., Wiley-Interscience. The protecting group may also be a polymer resin such as a Wang resin or a 2-chlorotrityl chloride resin.

It will also be appreciated by those skilled in the art, although such protected derivatives of compounds of formulae (I), (II) and (III), as described above in the Summary of the Invention, may not possess pharmacological activity as such, they may be administered to a mammal having a condition resulting from an abnormality in nitric oxide production and thereafter metabolized in the body to form compounds of the invention which are pharmacologically active. Such derivatives may therefore be described as "prodrugs". All prodrugs of compounds of formulae (I), (II) and (III) are included within the scope of the invention.

A. Preparation of Compounds of Formula (Ia)

Compounds of formula (Ia) are compounds of formula (I) as defined above in the Summary of the Invention and are prepared as illustrated below in Reaction Scheme 1 wherein $X^1$ is halo or halo-$(CH_2)_q$— (where q is defined as above in the Summary of the Invention); $X^2$ is halo; $A^1$ is —O—, —$(CH_2)_q$—O— (where q is defined as above in the Summary of the Invention and the oxygen is attached to the hydrogen) or —$(CH_2)_q$—$N(R^6)$— (where q is defined as above in the Summary of the Invention and the nitrogen is attached to the hydrogen); $R^1$, $R^2$, $R^3$ and $R^4$ are as defined above in the Summary of the Invention; m, n and p are as described above in the Summary of the Invention and PG is a nitrogen-protecting group, such as benzyl, benzyloxycarbonyl or t-butoxycarbonyl:

REACTION SCHEME 1

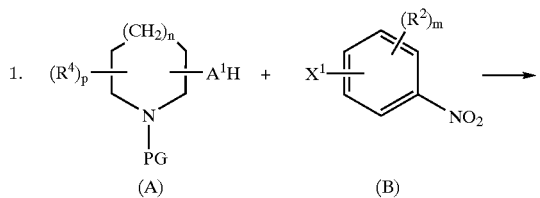

-continued

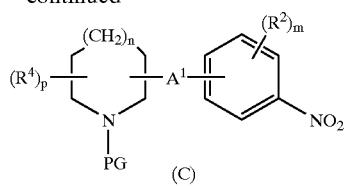
(C)

↓

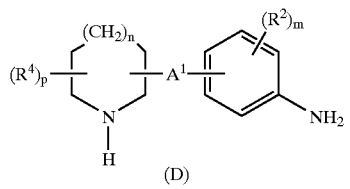
(D)

2. (D) + X²R¹ ⟶
       (E)

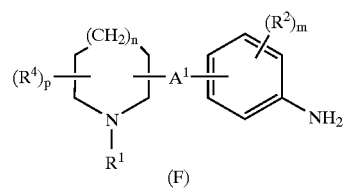
(F)

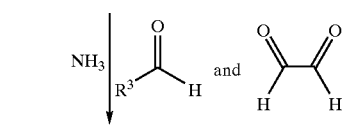

↓

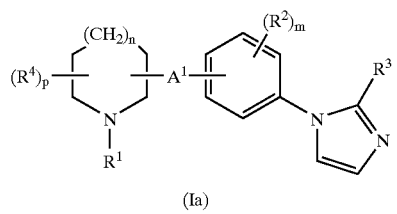
(Ia)

Compounds of formulae (A), (B) and (E) are commercially available, or may be prepared according to methods known to one of ordinary skill in the art.

In general, compounds of formula (Ia) are prepared by first treating a compound of formula (A) in an aprotic solvent, such as DMF, in the presence of a strong base, preferably sodium hydride, at ambient temperature, with a slightly excess molar amount of a compound of formula (B) in an aprotic solvent, such as DMF. The resulting mixture is stirred at temperatures of between about 0° C. and ambient temperature, preferably at ambient temperature, for a period of about 2 hours to about 12 hours, preferably for about 2 hours. The compound of formula (C) is isolated from the reaction mixture by standard isolation techniques, such as organic extraction and purification by silical gel chromatography.

The compound of formula (C) is then treated to standard reduction conditions, such as treatment with hydrogen in the presence of a palladium catalyst, to afford a compound of formula (D), which is isolated from the reaction mixture by standard isolation techniques, such as filtration and recrystallization in organic solvent.

The compound of formula (D) at a temperature of between about 0° C. and about 100° C., preferably at about 0° C., in an aprotic solvent, such as DMF, in the presence of a base, such as potassium carbonate, and an alkaline metal iodide, such as sodium iodide, and is then treated with a compound of formula (E). The resulting reaction mixture is stirred at a temperature of about 0° C. to about 100° C., preferably at ambient temperature, for a period of about 2 hours to about 12 hours, preferably for about 2 hours. The compound of formula (F) is isolated from the reaction mixture by standard isolation techniques, such as organic extraction and purification by column chromatography.

The compound of formula (F) is then treated under standard Debus reaction conditions, such as treatment with ammonium hydroxide in a protic solvent, such as methanol, and an aldehyde, such as formadehyde, and a dione, such as glyoxal, in a protic solvent, such as water, at temperatures of about 0° C. to about 100° C., preferably at about 65° C., for a period of about 2 hours to about 12 hours, preferably for about 2 hours. The compound of formula (Ia) is isolated from the reaction mixture by standard isolation techniques, such as evaporation of solvents, organic extraction and purification by column chromatography.

B. Preparation of Compounds of Formula (IIa)

Compounds of formula (IIa) are compounds of formula (II) as described above in the Summary of the Invention and are prepared as illustrated below in Reaction Scheme 2 wherein $X^1$ is halo or halo-$(CH_2)_q$— (where q is defined as above in the Summary of the Invention); $X^2$ is halo; $A^1$ is —O—, —$(CH_2)_q$—O— (where q is defined as above in the Summary of the Invention and the oxygen is attached to the hydrogen) or —$(CH_2)_q$—N($R^6$)— (where q is defined as above in the Summary of the Invention and the nitrogen is attached to the hydrogen); $R^1$, $R^2$, $R^3$ and $R^4$ are as defined above in the Summary of the Invention except that $R^4$ can not be hydroxy; m, n and p are as described above in the Summary of the Invention; and PG is nitrogen-protecting group:

REACTION SCHEME 2

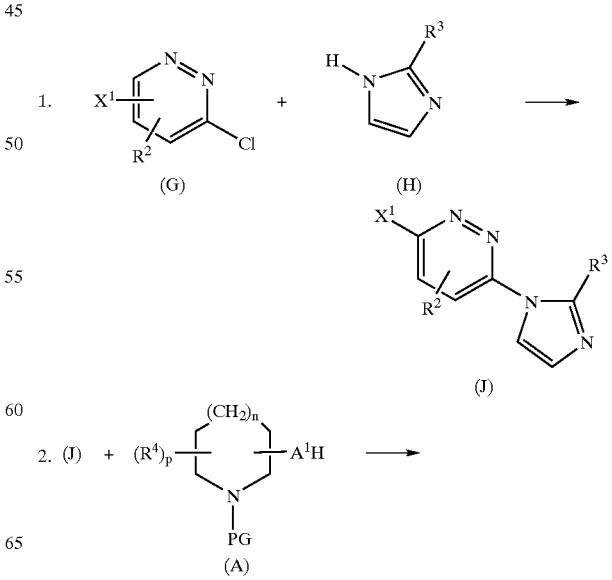

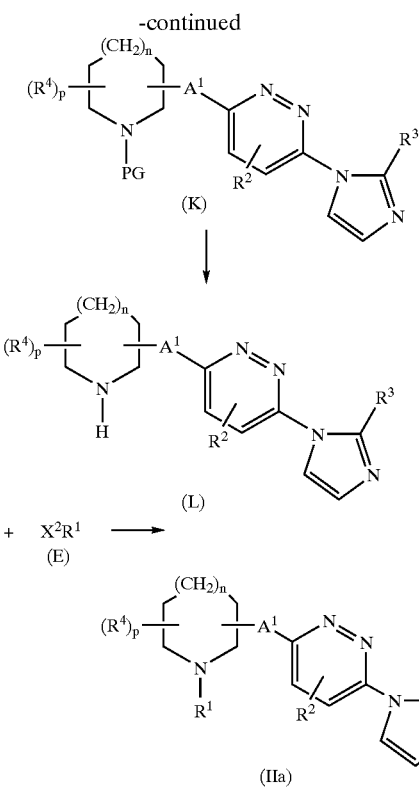

3. (L) + X²R¹ ⟶
      (E)

Compounds of formulae (G), (H), (A) and (E) are commercially available, or may be prepared according to methods known to one skilled in the art.

In general, compounds of formula (IIa) are prepared by first treating a mixture of a compound of formula (G) and an excess molar amount of a compound of formula (H) in an aprotic solvent, such as DMF, in the presence of a base, such as potassium carbonate, at a temperature of between about 0° C. and about 100° C., preferably at a temperature of between about 70° C. and 80° C., for a period of about 4 hours to about 18 hours, preferably for about 18 hours. The compound of formula (J) is isolated from the reaction mixture by standard isolation techniques, such as evaporation of solvent, organic extraction, and separation by column chromatography.

The compound of formula (J) in an aprotic solvent, such as DMF, is then treated with an equimolar amount of a compound of formula (A) in an aprotic solvent, such as DMF, in the presence of a strong base, such as sodium hydride, at a temperature of between about 0° C. and 100° C., preferably at ambient period, for a period of about 30 minutes to 2 hours, preferably for about 1 hour. The compound of formula (K) is then isolated from the reaction mixture by standard isolation techniques, such as evaporation of solvent, organic extraction and purification by column chromatography.

The compound of formula (K) is then de-protected under standard nitrogen deprotection conditions, such as treatment with a strong acid or base in the presence of a palladium catalyst, to form a compound of formula (L), which is isolated from the reaction mixture by standard isolation techniques.

The compound of formula (L) in an aprotic solvent, such as DMF, is then treated with an equivalent molar amount of a compound of formula (E) in the presence of a base, such as potassium carbonate, at a temperature of between about 0° C. and about 100° C., preferably at a temperature of about 50° C., for a period of about 2 hours to about 4 hours, preferably for about 3 hours. The compound of formula (IIa) is isolated from the reaction mixture by standard isolation techniques, such as filtration and concentration, organic extraction, and purification by column chromatography.

C. Preparation of Compounds of Formula (Ib)

Compounds of formula (Ib) are compounds of formula (I) as described above in the Summary of the Invention and are prepared as illustrated below in Reaction Scheme 3 wherein $X^2$ is halo; $A^1$ is —O—, —$(CH_2)_q$—O— (where q is defined as above in the Summary of the Invention and the oxygen is attached to the hydrogen) or —$(CH_2)_q$—N($R^6$)— (where q is defined as above in the Summary of the Invention and the nitrogen is attached to the hydrogen); $R^1$, $R^2$, $R^3$ and $R^4$ are as defined above in the Summary of the Invention except that $R^4$ can not be hydroxy; m, n, p, and q are as described above in the Summary of the Invention; and PG is nitrogen-protecting group:

REACTION SCHEME 3

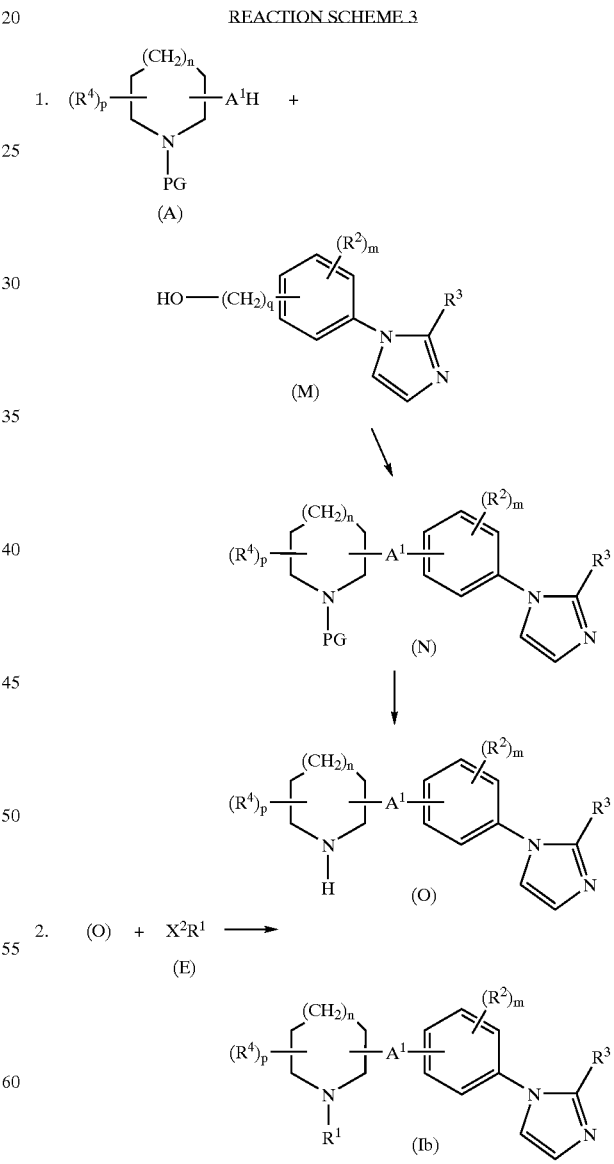

Compounds of formulae (A), (M) and (E) are commercially available, or may be prepared according to methods known to one skilled in the art.

In general, compounds of formula (Ib) are prepared by first treating a mixture of a compound of formula (A) and an excess molar amount of a compound of formula (M) in an aprotic solvent, such as DMF, to standard Mitsunobu Reaction conditions (see, Mitsunobu, O. et al., *Bull. Chem. Soc., Japan* (1967), Vol. 40, p. 2380), i.e., treatment with diethyl azodicarboxylate and triphenyl phosphine at ambient temperature. The compound of formula (N) is isolated from the reaction mixture by standard isolation techniques, such as evaporation of the solvent, organic extraction and purification by flash column chromatography.

The compound of formula (N) is then deprotected under standard acid hydrolysis conditions, such as treatment with trifluoroacetic acid for a t-butoxycarbonyl protected amine, to afford the compound of formula (O), which is isolated from the reaction mixture by standard isolation techniques.

Compounds of formula (O) are then treated with a compound of formula (E) in a manner similar to that described above for compounds of formula (Ia) and (IIa) to prepared compounds of formula (Ib), which is isolated from the reaction mixture by standard isolation techniques.

D. Preparation of Compounds of Formula (Ic)

Compounds of formula (Ic) are compounds of formula (I) as described above in the Summary of the Invention and are prepared as illustrated below in Reaction Scheme 3 wherein $X^2$ is halo; PG is a nitrogen protecting group such as benzyl or t-butoxycarbonyl; m, n, p and q, and $R^1$, $R^2$, $R^3$ and $R^6$ are as defined above in the Summary of the Invention:

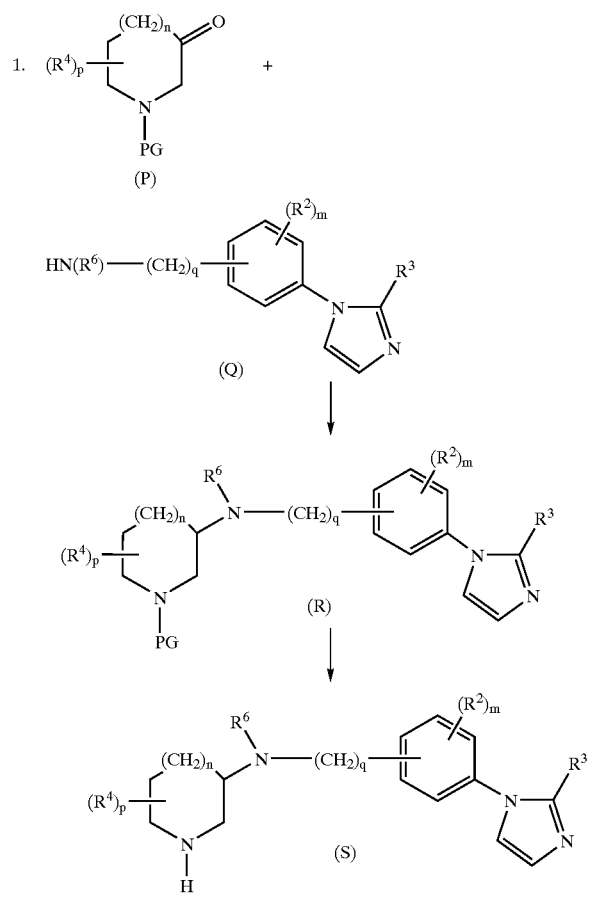

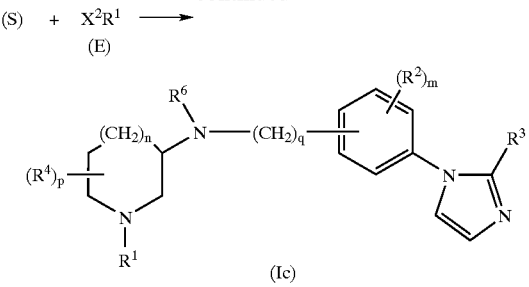

Compounds of formulae (P), (Q) and (E) are commercially available, or may be prepared according to methods known to one skilled in the art, or by methods disclosed herein.

In general, compounds of formula (Ic) are prepared by first treating a compound of formula (P) to standard reductive amination conditions, such as treating the compound of formula (P) with an equimolar amount of a compound of formula (Q) in the presence of an excess molar amount of a dehydrating agent, such as Ti(OiPr)$_4$. The resulting mixture is stirred at ambient temperature for a period of between about 30 minutes and about 2 hours, preferably for about 1.25 hours. The mixture is then diluted with a protic solvent, such as ethanol, and treated with a reducing reagent, such as sodium cyanoborohydride. The resulting mixture is stirred at ambient temperature for a period of between about 8 hours and about 24 hours, preferably for about 20 hours. The compound of formula (R) is isolated from the reaction mixture by standard isolation conditions, such as precipitation and flash column chromatography.

The compound of formula (R) is then deprotected by standard nitrogen deprotection techniques, such as hydrogenation in the presence of a palladium catalyst. The compound of formula (S) is isolated from the reaction mixture by standard isolation techniques, such as filtration and evaporation of solvents.

The compound of formula (S) is then treated with a compound of formula (E) under conditions similar to those described above for the treatment of compounds of formula (D) with compounds of formula (E) to form a compound of formula (Ic), which is isolated from the reaction mixture by standard isolation techniques.

E. Preparation of Compounds of Formula (Id)

Compounds of formula (Id) are compounds of formula (I) as described above in the Summary of the Invention and are prepared as illustrated below in Reaction Scheme 3 wherein m, n, p, $R^2$, $R^3$ and $R^4$ are as defined above in the Summary of the Invention; $A^1$ is as described above in the Summary of the Invention; and $R^{1a}$ is aryl optionally substituted by one or more substituents selected from the group consisting of alkyl, halo, haloalkyl, hydroxy, alkoxy, aralkoxy, aryl, aralkyl, amino, dialkylamino, monoalkylamino, nitro, carboxy, alkoxycarbonyl, aminocarbonyl, monoalkylaminocarbonyl and dialkylaminocarbonyl:

REACTION SCHEME 5

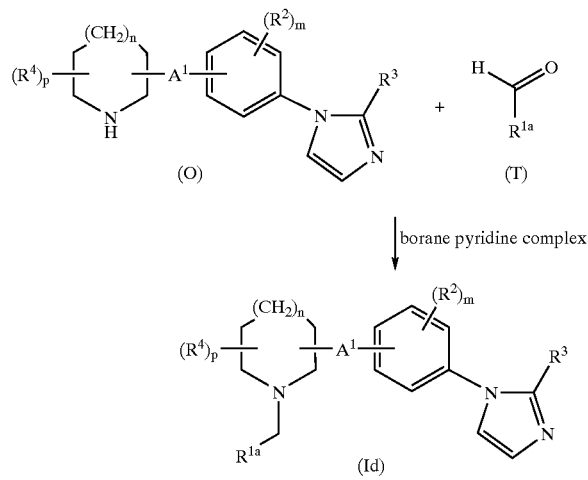

Compounds of formula (O) are prepared according to methods disclosed herein or by methods known to one of ordinary skill in the art. Compounds of formula (T) are commercially available or may be prepared according to methods known to one of ordinary skill in the art.

In general, compounds of formula (Id) are prepared by treating compounds of formula (O) and formula (T) to standard reductive amination conditions, such as treating a compound of formula (O) in a protic solvent, such as methanol, with an excess molar amount of a compound of formula (T) in the presence of a reducing reagent, such as a borane pyridine complex. The resulting mixture is stirred at ambient temperature for a period of between about 8 hours and about 24 hours, preferably for about 12 hours. The compound of formula (Id) is isolated from the reaction mixture by standard isolation techniques, such as evaporation of solvents, organic extraction and purification by flash column chromatography.

F. Preparation of Compounds of Formula (III)

Compounds of formula (III) are compounds of the invention as described above in the Summary of the Invention and are prepared as illustrated below in Reaction Scheme 6 wherein $A^2$ is —$(CH_2)_q$—O— (where q is 2 to 3); $X^2$ is halo; and m, $R^1$, $R^2$, $R^3$ and $R^6$ are as defined above in the Summary of the Invention:

REACTION SCHEME 6

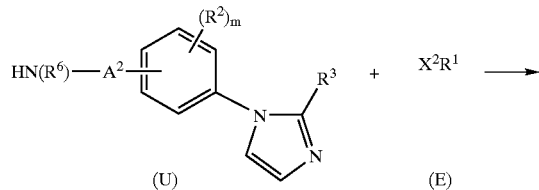

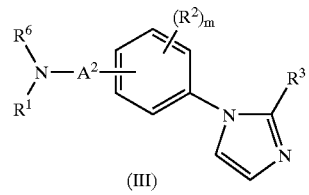

Compounds of formula (U) and formula (E) are commercially available, or may be prepared according to methods known to one skilled in the art.

In general, compounds of formula (III) are prepared by first treating a compound of formula (U) to standard reductive amination conditions, such as first treating the compound of formula (U) in a protic solvent, such as methanol, with an equimolar amount of a compound of formula (E) in the presence of an acid, such as acetic acid. The reaction mixture is stirred at ambient temperature for a period of between about 30 minutes and about 2 hours, preferably for about 1 hour. An excess molar amount of sodium cyanoborohydride is then added to the reaction mixture and resulting mixture is allowed to stir at ambient temperature for a period of between about 12 hours and about 18 hours, preferably for about 18 hours. The compound of formula (III) is then isolated from the reaction mixture by standard isolation techniques, such as evaporation of solvents and chromatography.

All compounds of the invention as prepared above which exist in free base or acid form may be converted to their pharmaceutically acceptable salts by treatment with the appropriate inorganic or organic base or acid. Salts of the compounds prepared above may be converted to their free base or acid form by standard techniques. It is understood that all polymorphs, amorphous forms, anhydrates, hydrates, solvates and salts of the compounds of the invention are intended to be within the scope of the invention.

In the following Preparations and Examples, the following abbreviations and acronyms may be used: DEAD for diethyl azodicarboxylate; DIEA for diisopropylethylamine; DMF for dimethylformamide; THF for tetrahydrofuran; TFA for trifluoroacetic acid; DMAP for dimethylaminopyridine; $CH_3CN$ for acetonitrile; $CH_2Cl_2$ for dichloromethane (methylene choride); $CHCl_3$ for chloroform; DMSO for dimethyl sulfoxide; $Et_2O$ for diethyl ether; EDC or EDCl for 1-(3-dimethylaminopropyl)-3-ethylcarbodiimide hydrochloride; MeOH for methanol; BSA for bovine serum albumin; and HCl for hydrogen chloride.

The following specific Preparations (which are directed primarily to intermediates) and Examples (which are directed primarily to claimed compounds, pharmaceutical compositions and methods of use) are provided as a guide to assist in the practice of the invention, and are not intended as a limitation on the scope of the invention.

PREPARATION 1

Compounds of Formula (C)

A. To a suspension of NaH (0.83 g, 37 mmol) in DMF (10 mL) was added 1-benzyl-(3S)-3-hydroxypiperidine (4.1 g, 21.5 mmol), and the resulting reaction mixture was stirred at ambient temperature for 2 hours. 4-Fluoronitrobenzene (2.5 mL, 23.6 mmol) in DMF (10 mL) was then added to the mixture dropwise. The resulting reaction mixture was stirred at ambient temperature for 2 hours. After removal of DMF in vacuo, the crude mixture was dissolved in ethyl acetate (200 mL), washed with water (100 mL×3), brine (100 mL), to give a yellow oil. Purification using silical gel chromatography column afforded 1-benzyl-(3S)-3-(4-nitrophenoxy)piperidine (6.5 g, 97% yield) as a yellow oil.

B. In a similar manner, other compounds of formula (C) were prepared.

PREPARATION 2

Compounds of Formula (D)

A. A mixture of 1-benzyl-(3S)-3-(4-nitrophenoxy) piperidine (6.5 g) and 1.2 g of 10% Pd/C in methanol (30 mL) was subjected to hydrogenation (50 psi). When the reaction was completed, the reaction mixture was filtered. The filtrate was concentrated in vacuo, giving a yellow solid. Recrystallization in $CH_2Cl_2$/hexane afforded (3S)-3-(4-aminophenoxy)piperidine (3.5 g, 88% yield) as a white solid.

B. In a similar manner, other compounds of formula (D) were prepared.

PREPARATION 3

Compounds of Formula (F)

A. To an ice water-cooled solution of (3S)-3-(4-aminophenoxy)piperidine (3.5 g) in DMF (20 mL) was added $K_2CO_3$ (7.5 g) and NaI (0.2 g), followed by the addition of 5-chloromethyl-1,3-benzodioxole (4.7 mL). The resulting reaction mixture was stirred at ambient temperature for 2 hours. The reaction mixture was diluted with ethyl acetate (200 mL), washed with water (100 mL×3) and brine (100 mL), and dried ($Na_2SO_4$). The crude product was further purified by column chromatography (methanol:ethyl acetate1:10), to afford (3S)-3-(4-aminophenoxy)-1-[(1,3-benzodioxol-5-yl)methyl]piperidine (4.4 g, 74% yield) as an oil.

B. In a similar manner, other compounds of formula (F) were prepared.

PREPARATION 4

Compounds of Formula (J)

A. A mixture of imidazole (0.613 g, 8 mmol) and 3,6-dichloropyridazine (1.55 g, 10 mmol), $K_2CO_3$ (4.15 g) and DMF (15 mL) was heated at 70–80° C. overnight. After removal of DMF in vacuo, the residual solid was dissolved in $CH_2Cl_2$ (50 mL), washed with 1N $Na_2CO_3$ aq. solution, and dried ($MgSO_4$). Separation using column chromatography ($CH_2Cl_2$/methanol 100:1) afforded 3-chloro-6-(imidazol-1-yl)pyridazine (1.2 g) as a white solid.

B. In a similar manner, other compounds of formula (J) were prepared.

PREPARATION 5

Compounds of Formula (K)

A. To a suspension of NaH (0.21 g, 8.31 mmol) in DMF (5 mL) was added 1-benzyl-3-hydroxypiperidine hydrochloride (0.78 g, 3.3 mmol) in DMF (5 mL), and the resulting reaction mixture was stirred at ambient temperature for 30 minutes. 3-chloro-6-(imidazol-1-yl)pyridazine (0.6 g, 3.3 mmol) in DMF (5 mL) was then added dropwise. The reaction mixture was stirred at ambient temperature for 30 minutes. After removal of DMF in vacuo, the black oil was dissolved in $CH_2Cl_2$ (50 mL), washed with water and brine. Purification using column chromatography afforded 3-[(6-(imidazol-1-yl)pyridazin-3-yl)oxy]-1-benzylpiperidine (400 mg) as a yellow oil.

B. In a similar manner, other compounds of formula (K) were prepared.

PREPARATION 6

Compounds of Formula (L)

A. To a solution of 3-[(6-(imidazol-1-yl)pyridazin-3-yl)oxy]-1-benzylpiperidine (400 mg) in methanol (20 mL) was added 10% Pd/C (0.4 g), and $HCO_2NH_4$ (0.6 g). The mixture was heated at reflux under $N_2$ for 1 hour. After cooling to ambient temperature, Pd/C was filtered off. The filtrate was concentrated in vacuo, giving 3-[(6-(imidazol-1-yl) pyridazin-3-yl)oxy]piperidine (240 mg) as an oil, which was used in Example 3 without further purification.

B. In a similar manner, other compounds of formula (L) were prepared.

PREPARATION 8

Compounds of formula (N) and formula (O)

A. To a mixture of (3R)-1-t-butoxycarbonyl-3-hydroxypiperidine (4.10 g, 17.8 mmol), 4-(imidazol-1-yl) phenol (4.4 g, 1.5 eq.), triphenylphosphine (1.5 eq., 7.10 g), DMF (80 mL) was added DEAD (1.5 eq., 4.33 mL). The resulting reaction mixture were stirred at room temperature for two days. The solvent was evaporated, the residue was diluted with ethyl acetate, washed with 1N NaOH (45 mL×3), water and brine, and evaporated in vacuo. Purification by flash column chromatography on silical gel with gradient 1–3% methanol in $CH_2Cl_2$ gave (3R)-1-t-butoxycarbonyl-3-[4-(imidazol-1-yl)phenoxy]piperidine (420 mg, 1.19 mmol), which was treated with trifluoroacetic acid/$CH_2Cl_2$ (1:1) from 0° C. to ambient temperature for 2 hours. The solvents were evaporated. The residue was diluted with $CH_2Cl_2$, and washed with 1N HCl (10 mL). The aqueous phase was extracted with $CH_2Cl_2$ to remove by-product. The aqueous phase was re-adjusted to pH 9.5 to 10.0 with 1N NaOH. Extraction with $CH_2Cl_2$ (60 mL×3) and evaporation of the solvent in vacuo gave (3R)-3-[4-(imidazol-1-yl)phenoxy]piperidine (62 mg) as an oil.

B. In a similar manner, other compounds of formula (O) were prepared.

PREPARATION 9

Compounds of Formula (R) and Formula (S)

A. 1-Benzyl-3-piperidinone (2.07 g, 10 mmol), 4-(imidazol-1-yl)aniline (1.73 g, 1.0 eq.), and $Ti(OiPr)_4$ (3.72 mL, 1.25 eq.) were stirred at ambient temperature for 1.25 hours. The mixture was then diluted with absolute ethanol (10 mL) and $NaCNBH_3$ (0.44 g, 0.67 eq.) was added. The resulting mixture was stirred for 20 hours. Water (2 mL) was added to the mixture with stirring and the resulting precipitate was filtered. Flash column chromatography on silical gel with 1–5% methanol in methylene chloride gave a crude product. Further purification by HPLC afforded 3-[(4-(imidazol-1-yl)phenyl)amino]-1-benzylpiperidine (569 mg), which was dissolved in methanol (10 mL) and treated with 10% Pd/C (400 mg) and ammonium formate (800 mg). The resulting mixture was heated at reflux for 4 hours. After cooling to ambient temperature, the mixture was filtered. Evaporation of the solvent in vacuo gave 3-[(4-(imidazol-1-yl)phenyl)amino]piperidine (330 mg, 1.36 mmol).

B. In a similar manner, other compounds of formula (S) are prepared.

EXAMPLE 1

Compounds of Formula (I)

A. Solution A was prepared by adding (3S)-3-(4-aminophenoxy)-1-[(1,3-benzodioxol-5-yl)methyl]piperidine (4.4 g, 13.5 mmol) and NH$_4$OH (1.2 mL, 15 mmol) in methanol, and diluting with methanol to 10 mL. Solution B was prepared by adding formaldehyde (1.01 mL, 13.5 mmol) and 40% solution glyoxal, and then diluting with THF to 10 mL. Solution A and solution B were added simultaneously to water (6.0 mL, pre-heated to 65° C.) with stirring over a 30 min period. The resulting mixture was then heated to 65° C. for 2 hours. After removal of the solvent in vacuo, the residual oil was dissolved in CH$_2$Cl$_2$ (100 mL), washed with water (50 mL×3), brine (50 mL), and dried (NaSO$_4$). Purification by column chromatography (ethyl acetate/methanol 100:1) afforded (3S)-3-[4-(imidazol-1-yl)phenoxy]-1-[(1,3-benzodioxol-5-yl)methyl]piperidine (3.7 g, 72.5% yield), NMR: (DMSO-d6) 9.1 (s, 1), 7.90 (t, 1), 7.65–7.62 (m, 2), 7.56 t, 1), 7.32 (d, 1), 7.24–7.21 (m, 2), 7.10 (d, 1), 6.98 (d, 1), 5.98 (d, 2), 5.00 (m, 1), 4.28 (d, 1), 4.18 (d, 1), 3.40 (d, 1), 3.12 (m, 1), 3.09–2.98 (m, 2), 2.05–1.88 (m, 3), 1.72 (m, 1) ppm.

B. In a similar manner, the following compounds of formula (I) were prepared:
(3R)-3-[4-(imidazol-1-yl)phenoxy]-1-[(1,3-benzodioxol-5-yl)methyl]piperidine, $^1$H NMR (CDCl$_3$) 7.77 (s, 1), 7.28–7.22 (m, 3), 7.18 (d, 1), 6.96 (d, 2), 6.82 (s, 1), 6.72 (s, 2), 5.93 (s, 2), 4.38 (m, 1), 3.47 (s, 2), 3.01 (d, 1), 2.70 (m, 1), 2.20–2.02 (m, 3), 1.84–1.40 (m, 3) ppm.

C. In a similar manner, other compounds of formula (I) are prepared.

EXAMPLE 2

Compounds of Formula (II)

A. A mixture of 3-[(6-(imidazol-1-yl)pyridazin-3-yl)oxy]piperidine (220 mg), 5-chloromethyl-1,3-benzodioxole (0.26 mL), K$_2$CO$_3$ (1.0 g), and NaI (0.1 g) in DMF (15 mL) was heated at 50° C. under N$_2$ for 3 hours. After filtration and concentration in vacuo, the residual oil was dissolved in CH$_2$Cl$_2$ (100 mL), washed with water (20 mL×3) and brine, dried (MgSO$_4$), and concentrated. Purification by column chromatography gave 3-[(6-(imidazol-1-yl)pyridazin-3-yl)oxy]-1-[(1,3-benzodioxol-5-yl)methyl]piperdine, (77 mg) as a white solid, NMR: (CDCl$_3$) 8.30 (s, 1), 7.68 (s, 1), 7.52 (d, 1), 7.22 (s, 1), 7.16 (d, 1), 6.75 (s, 2), 5.90 (d, 2), 5.41 (m, 1), 3.46 (Abq, 2), 2.88 (d, 1), 2.58–2.48 (m, 2), 2.32 (m, 1), 2.10 (m, 1), 1.70–1.60 (m, 2) ppm.

B. In a similar manner, the following compound of formula (II) was prepared:
2-[((6-(imidazol-1-yl)pyridazin-3-yl)oxy)methyl]-1-[(1,3-benzodioxol-5-yl)methyl]piperidine, $^1$H NMR (CDCl$_3$) 8.28 (s, 1), 7.68 (s, 1), 7.52 (d, 2), 7.24 (s, 1), 7.19 (d, 2), 6.93 (s, 1), 6.76–6.68 (m, 2), 5.90 (s, 2), 4.70 (d, 2), 3.98 (d, 1), 3.37 (d, 1), 2.80 (m, 2), 2.18 (m, 1), 1.84–1.38 (m, 5) ppm.

C. In a similar manner, other compounds of formula (II) are prepared.

EXAMPLE 3

Compounds of Formula (I)

A. (3R)-3-[4-(Imidazol-1-yl)phenoxy]piperidine (150 mg, 0.61 mmol) was dissolved in DMF (2 mL) and was added to a solution of 5-chloromethyl-1,3-benzodioxole (0.16 ml in 50% methylene chloride, 1.0 eq.) in DMF, followed by the addition of K$_2$CO$_3$ (2.5 eq.) and NaI (0.1 eq.). The resulting mixture was heated at 50° C. for 1 hour. The solvent was evaporated and flash column chromatography on silical gel with 3% methanol in methylene chloride gave a crude product (112 mg). Additional flash chromatography with 3% methanol in ethyl acetate afforded (3R)-3-[4-(imidazol-1-yl)phenoxy]-1-[(1,3-benzodioxol-5-yl)methyl]piperidine (70 mg), $^1$H NMR (CDCl$_3$) 7.75 (s, 1), 7.30 (d, 2), 7.20 (d, 2), 7.00 (d, 2), 6.85 (s, 1), 6.75 (d, 2), 5.90 (s, 2), 4.40 (m, 1), 3.50 (s, 2), 3.00 (m, 1), 2.70 (m, 1), 2.20 (m, 3), 1.85 (m, 1), 1.50 (m, 2) ppm.

B. In a similar manner, the following compounds of formula (I) were prepared:
3-[4-(imidazol-1-yl)phenoxy]-1-[(1,3-benzodioxol-5-yl)methyl]piperidine, trifluoroacetic acid salt, $^1$H NMR (DMSO-d$_6$) 9.60 (m, 1), 8.20 (m, 1), 7.90 (s, 1), 7.70 (m, 2), 7.20 (m, 3), 7.00 (m, 2), 6.00 (s, 2), 4.50 (m, 1), 4.30 (m, 2), 4.00 (m, 1), 3.30 (m, 2), 3.00 (m, 1), 2.30 (m, 1), 1.70–2.00 (m, 3) ppm;

(3R)-3-[4-(imidazol-1-yl)phenoxy]-1-[(1,3-benzodioxol-5-yl)methyl]piperidine, $^1$H NMR(DMSO-d$_6$) 9.60 (m, 1), 8.20 (m, 1), 7.90 (s, 1), 7.70 (m, 2), 7.00–7.30 (m, 5), 6.0 (s, 2), 4.50 (m, 1), 4.30 (m, 2), 4.00 (m, 1), 3.20–3.40 (m, 2), 3.00 (m, 1), 2.30 (m, 1), 1.70–2.00 (m, 3) ppm;

3-[4-(imidazol-1-yl)phenoxy]-1-[(1,3-benzodioxol-5-yl)methyl]piperidine, $^1$H NMR(CDCl$_3$) 7.74 (s, 1), 7.25 (d, 2), 7.16 (s, 2), 6.94 (d, 2), 6.82 (s, 1), 6.71 (s, 2), 5.90 (s, 2), 4.35 (m, 1), 3.45 (AB q, 2), 3.00 (m, 1), 2.70 (m, 1), 2.10–2.38 (m, 3), 1.45 (m, 2) ppm;

3-[4-(imidazol-1-yl)phenoxy]-1-(3,4-dimethoxybenzyl)piperidine, $^1$H NMR(CDCl$_3$) 7.80 (s, 1), 7.30 (m, 3), 7.20 (d, 2), 7.00 (d, 2), 6.80 (m, 2), 4.40 (m, 1), 3.90 (s, 6), 3.50 (AB q, 2), 3.00 (m, 1), 2.70 (m, 1), 2.10–2.30 (m, 3), 1.80 (m, 2), 1.50 (m, 2) ppm;

3-[(4-(imidazol-1-yl)phenoxy)methyl]-1-[(1,3-benzodioxol-5-yl)methyl]piperidine, $^1$H NMR(CDCl$_3$) 7.80 (s, 1), 7.30 (d, 2), 7.20 (d, 2), 6.95 (d, 2), 6.85 (s, 1), 6.75 (s, 2), 5.95 (s, 2), 3.80 (d, 2), 3.40 (AB q, 2), 2.90 (m, 1), 2,70 (m, 1), 2.20 (m, 1), 1.70 (m, 3), 1.20 (m, 1) ppm;

2-[(4-(imidazol-1-yl)phenoxy)methyl]-1-[(1,3-benzodioxol-5-yl)methyl]piperidine, $^1$H NMR(CDCl$_3$) 7.75 (s, 1), 7.30 (d, 2), 7.20 (d, 2), 7.00 (d, 2), 6.90 (s, 1), 6.70 (m, 2), 5.90 (s, 2), 4.20 (m, 1), 4.00 (m, 2), 3.36 (m, 1), 2,80 (m, 1), 2.20 (m, 1), 1.40–1.90 (m, 6) ppm;

3-[4-(imidazol-1-yl)phenoxy]-1-[(1,3-benzodioxol-5-yl)methyl]hexahydro-1H-azepine, $^1$H NMR(CDCl$_3$) 7.70 (s, 1), 7.10 (m, 4), 6.90 (s, 1), 6.60–6.80 (m, 4), 5.90 (s, 2), 4.30 (m, 1), 3.50 (AB q, 2), 2.80 (m, 2), 2.60 (m, 2), 2.10 (m, 1), 1.60–1.80 (m, 5) ppm;

3-[4-(imidazol-1-yl)phenoxy]-1-[(1,3-benzodioxol-5-yl)carbonyl]pyrrolidine, $^1$H NMR (CDCl$_3$) 7.63 (s, 1), 7.22–6.80 (m, 8), 6.66 (d, 1), 5.82 (s, 2), 4.86 (m, 1), 3.90–3.50 (m, 4), 2.18–2.05 (m, 2) ppm;

(3S)-3-[4-(imidazol-1-yl)phenoxy]-1-[(1,3-benzodioxol-5-yl)methyl]pyrrolidine, $^1$H NMR (CDCl$_3$) 7.74 (s, 1), 7.24–7.22 (m, 3), 7.16 (d, 2), 6.88 (d, 2), 6.83 (s, 1), 6.76–6.73 (m, 2), 5.92 (s, 2), 4.80 (m, 1), 3.95 (d, 1), 3.54 (d, 1), 2.92 (m, 1), 2.78–2.68 (m, 2), 2.58 (m, 1), 2.15 (m, 1), 1.98 (m, 1) ppm; and 3-[4-(imidazol-1-yl)phenoxy]-1-[(1,3-benzodioxol-5-yl)methyl]pyrrolidine, $^1$H NMR (CDCl$_3$) 7.62 (s, 1), 7.17 (d, 2), 7.08 (d, 2), 6.81–6.78 (m, 3), 6.68–6.61 (m, 2), 5.80 (s, 2), 4.73 (m, 1), 3.48 (AB q, 2), 2.84 (m, 1), 2.70–2.62 (m,2), 2.48 (m, 1), 2.21 (m, 1), 1.88 (m, 1) ppm.

C. In a similar manner, other compounds of formula (I) are prepared.

EXAMPLE 4

Compounds of Formula (I)

A. 3-[(4-(Imidazol-1-yl)phenyl)amino]piperidine (330 mg, 1.36 mmol) was dissolved in DMF and then treated with 5-chloromethyl-1,3-benzodioxole (1.0 eq.), $K_2CO_3$ (2.5 eq.) and NaI (0.1 eq.). The resulting mixture was heated at 50° C. for 1 hour. Filtration of the mixture and evaporation of the solvent in vacuo gave a crude product (411 mg). Flash column chromatography on silical gel with 1–2.5% methanol in methylene chloride afforded 3-[(4-(imidazol-1-yl)phenyl)amino]-1-[(1,3-benzodioxol-5-yl)methyl]piperidine (110 mg), $^1$H NMR(CDCl$_3$) 7.70 (s, 1), 7.10 (m, 4), 6.80 (s, 1), 6.70 (m, 2), 6.60 (d, 2), 5.90 (s, 2), 4.30 (m, 1), 3.60 (m, 1), 3.40 (AB q, 2), 2.70 (m, 1), 2.40 (m, 3), 1.50–1.80 (m, 4) ppm.

B. In a similar manner, other compounds of formula (I) are prepared.

EXAMPLE 5

Compounds of Formula (I)

A. To a mixture of 3-[4-(imidazol-1-yl)phenoxy]piperidine (308 mg, 1.26 mmol), methanol (6.0 mL) was added 4-methoxy-1-naphthaldehyde (1.25 eq, 298 mg), followed by borane pyridine complex (0.196 mL, 1.25 eq.). The resulting mixture was stirred overnight. The methanol was evaporated, and the residue diluted with ethyl acetate, washed with water and brine. Evaporation of the solvent in vacuo gave a crude product. Flash column chromatography on silical gel with 1–2% methanol in methylene chloride afforded 3-[4-(imidazol-1-yl)phenoxy]-1-[(4-methoxynaphth-1-yl)methyl]piperidine (54 mg), $^1$H NMR (CDCl$_3$) 8.30 (m, 2), 7.70 (s, 1), 7.50 (m, 2), 7.30 (s, 1), 7.20 (m, 4), 6.90 (m, 2), 6.70 (d, 2), 4.30 (m, 1), 4.00 (s, 3), 3.90 (AB q , 2), 3.10 (m, 1), 2.80 (m, 1), 2.10–2.30 (m, 3), 1.80 (m, 1), 1.40–1.70 (m, 2) ppm.

B. In a similar manner, other compounds of formula (I) are prepared.

EXAMPLE 6

Compound of Formula (III)

A. To 2-[4-(imidazol-1-yl)phenoxy]ethylamine (4.0 g, 20 mmol) dissolved in MeOH (150 mL) was added piperonal (3.0 g, 20 mmol) and acetic acid (1.5 mL). After stirring for 1 h, NaBH$_3$CN (2.6 g, 40 mmol) was added. After stirring for 18 hour, the solvent was removed in vacuo and the residue was chromatographed on silical gel with 2% methanol in methylene chloride to give 3.5 g of N-[2-(4-(imidazol-1-yl)phenoxy)ethyl]-N-[(1,3-benzodioxol-5-yl)methyl]amine, $^1$H NMR (DMSO-d$_6$) 8.12 (s, 1), 7.62 (s, 1), 7.54 (d, 2), 7.08–7.02 (m, 3), 6.90 (s, 1), 6.82–6.75 (m, 2), 5.94 (s, 2), 4.03 (t, 2), 3.62 (s, 2), 3.32 (s, 1), 2.80 (t, 2) ppm.

B. In a similar manner, the following compounds of formula (III) were prepared:

N-(carboxymethyl)-N-[2-(4-(imidazol-1-yl)phenoxy)ethyl]-N-[(1,3-benzodioxol-5-yl)methyl]amine;

N-(ethoxycarbonylmethyl)-N-[2-(4-(imidazol-1-yl)phenoxy)ethyl]-N-[(1,3-benzodioxol-5-yl)methyl]amine;

N-[2-(4-(imidazol-1-yl)phenoxy)ethyl]-N,N-di[(1,3-benzodioxol-5-yl)methyl]amine;

N-[(((3-(2-methylpiperidin-1-yl)propyl)amino)carbonyl)methyl]-N-[2-(4-(imidazol-1-yl)phenoxy)ethyl]-N-[(1,3-benzodioxol-5-yl)methyl]amine;

[((((1,3-benzodioxol-5-yl)methyl)amino)carbonyl)methyl]-N-[2-(4-(imidazol-1-yl)phenoxy)ethyl]-N-[(1,3-benzodioxol-5-yl)methyl]amine;

N-[((((4-trifluoromethylphenyl)methyl)amino)carbonyl)methyl]-N-[2-(4-(imidazol-1-yl)phenoxy)ethyl]-N-[(1,3-benzodioxol-5-yl)methyl]amine; and N-[(((butyl)amino)carbonyl)methyl]-N-[2-(4-(imidazol-1-yl)phenoxy)ethyl]-N-[(1,3-benzodioxol-5-yl)methyl]amine.

EXAMPLE 7

This example illustrates the preparation of representative pharmaceutical compositions for oral administration containing a compound of the invention, or a pharmaceutically acceptable salt thereof:

| A. | Ingredients | % wt./wt. |
|---|---|---|
| | Compound of the invention | 20.0% |
| | Lactose | 79.5% |
| | Magnesium stearate | 0.5% |

The above ingredients are mixed and dispensed into hard-shell gelatin capsules containing 100 mg each, one capsule would approximate a total daily dosage.

| B. | Ingredients | % wt./wt. |
|---|---|---|
| | Compound of the invention | 20.0% |
| | Magnesium stearate | 0.9% |
| | Starch | 8.6% |
| | Lactose | 69.6% |
| | PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. | Ingredients | |
|---|---|---|
| | Compound of the invention | 0.1 g |
| | Propylene glycol | 20.0 g |
| | Polyethylene glycol 400 | 20.0 g |
| | Polysorbate 80 | 1.0 g |
| | Water | q.s. 100 mL |

The compound of the invention is dissolved in propylene glycol, polyethylene glycol 400 and polysorbate 80. A sufficient quantity of water is then added with stirring to provide 100 mL of the solution which is filtered and bottled.

| D. | Ingredients | % wt./wt. |
|---|---|---|
| | Compound of the invention | 20.0% |
| | Peanut Oil | 78.0% |
| | Span 60 | 2.0% |

The above ingredients are melted, mixed and filled into soft elastic capsules.

| E. | Ingredients | % wt./wt. |
|---|---|---|
| | Compound of the invention | 1.0% |
| | Methyl or carboxymethyl cellulose | 2.0% |
| | 0.9% saline | q.s. 100 mL |

The compound of the invention is dissolved in the cellulose/saline solution, filtered and bottled for use.

EXAMPLE 8

This example illustrates the preparation of a representative pharmaceutical formulation for parenteral administration containing a compound of the invention, or a pharmaceutically acceptable salt thereof:

| Ingredients | |
|---|---|
| Compound of the invention | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution which is filtered through a 0.2 m membrane filter and packaged under sterile conditions.

EXAMPLE 9

This example illustrates the preparation of a representative pharmaceutical composition in suppository form containing a compound of the invention, or a pharmaceutically acceptable salt thereof:

| Ingredients | % wt./wt. |
|---|---|
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 10

This example illustrates the preparation of a representative pharmaceutical formulation for insufflation containing a compound of the invention, or a pharmaceutically acceptable salt thereof:

| Ingredients | % wt./wt. |
|---|---|
| Micronized compound of the invention | 1.0% |
| Micronized lactose | 99.0% |

The ingredients are milled, mixed, and packaged in an insufflator equipped with a dosing pump.

EXAMPLE 11

This example illustrates the preparation of a representative pharmaceutical formulation in nebulized form containing a compound of the invention, or a pharmaceutically acceptable salt thereof:

| Ingredients | % wt./wt. |
|---|---|
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

EXAMPLE 12

This example illustrates the preparation of a representative pharmaceutical formulation in aerosol form containing a compound of the invention, or a pharmaceutically acceptable salt thereof:

| Ingredients | % wt./wt. |
|---|---|
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fitted with a metering valve.

EXAMPLE 13

In Vitro Assay
Induction of iNOS in RAW 264.7 Mouse Monocytes

RAW 264.7 murine macrophage cells were obtained from American Type Culture Collection (Rockville, Md.) and were maintained in RPMI 1640 containing 10% fetal bovine serum (FBS), 5000 units/mL of penicillin and streptomycin, and 2 mM glutamine (maintenance medium). NOS activity was measured by a fluorescent assay of the nitric oxide oxidation product, nitrite (Diamani et al., *Talanta* (1986), Vol. 33, pp. 649–652). Induction of iNOS (inducible nitric oxide synthase) is stimulated by treatment of the cells with lipopolysaccharide and γ-interferon. The assay is described in more detail below.

Cells were harvested, diluted to 500,000 cells/mL with maintenance medium, and seeded into 96-well plates at 100 μL/well. The plates were incubated overnight at 37° C., under a 5% $CO_2$ atmosphere. The medium was then replaced with 90 μL of BME medium containing 10% FBS, 100 units/mL of penicillin, 100 μL streptomycin, 2 mM glutamine, 100 units/mL of γ-interferon and 2 μg/mL of lipopolysaccharide. N-guanidino-methyl-L-arginine was added to four wells (negative control) at a final concentration of 200 μM using 10 μL of 2 mM stock solution in 100 mM Hepes, pH 7.3+0.1% DMSO and four wells received only the 100 mM Hepes/0.1% DMSO buffer (positive control). Compounds of the invention were dissolved at 10-fold the desired final concentration in Hepes/DMSO and 10 μL of these solutions was transferred to the 96-well plate. The plates were incubated for 17 hrs at 37° C., under a 5% $CO_2$ atmosphere. Nitrite accumulation in the culture medium was determined as follows: To each well was added 15 μL of 2,3-diaminonaphthalene (10:g/mL in 0.75 M HCl) and each well was then incubated for 10 minutes at room temperature. To each well was then added 15 μL of 1 N NaOH and the fluorescence emission was measured at 405 nm, using an excitation wavelength of 365 nm. Enzyme activity in the experimental wells was normalized to percent control using the positive and negative control values. The signal to noise ratio was >10 for the assay.

The compounds of the invention, when tested in this assay, demonstrated the ability to inhibit nitric oxide production in vitro.

EXAMPLE 14

In Vitro Assay

A. A172 cells were obtained from the American Type Culture Collection, and were cultured routinely in DMEM without phenol red or sodium pyruvate but containing high glucose (Gibco BRL), supplemented with 10% (v/v) fetal bovine serum (Gibco BRL), in a humidified atmosphere of 5% $CO_2$ in air at 37° C. Cells were harvested and plated at 100,000 cells/well into 96-well tissue culture dishes in a total of 100 μL of culture medium. 18–24 hours later, inducible nitric oxide synthase (iNOS) activity was induced by the addition of 222 U/ml human interferon-gamma, 22 ng/ml of human tumor necrosis factor-alpha, and 2.2 ng/mL of human interleukin 1-β. All cytokines were purchased from Boehringer Mannheim. Concomitant with cytokine addition, the appropriate concentration of the compound of the invention was also added. Compound stock solutions were prepared in DMSO, and vehicle was added to control wells. Final concentration of DMSO in the incubations was less than 0.2%, and had no influence on iNOS induction or activity measurements. Incubations were continued for 18–24 hours, at which time an aliquot of the culture medium was removed and tested for nitrite concentration using the Griess reagent (see below).

B. Following incubation with cytokines plus compound, a 100 μL aliquot of the culture medium was removed and mixed with 150 μL of the Griess reagent (5% v/v phosphoric acid containing 2% w/v sulfanilamide plus 0.2% w/v naphthylethylenediamine) in a separate 96-well plate. The plates were read within 15 min at 550 nm in a SpectraMax spectrophotometer. The inhibition of iNOS activity by compound resulted in a decrease in the OD550 of the medium. $IC_{50}$ values were calculated from a log-logit analysis of the data. Inhibition curves with Hill slopes of less than 0.5 or greater than 1.5 were rejected.

Control experiments showed that no significant conversion of nitrite to nitrate occurred over the course of an experiment. Cells incubated in the absence of cytokines produced no measurable nitrite. Therefore, measuring the nitrite content of the culture medium of cytokine-induced cells is a simple, accurate means of measuring the induction of iNOS activity in these cells.

Compounds of the invention, when tested in this assay, demonstrated the ability to inhibit nitric oxide production in vitro.

EXAMPLE 15

In Vivo Assay

Effects of Compounds of the Invention on Adjuvant-Induced Arthritis in Rats

Male Lewis rats are injected intradermally (proximal quarter of the tail) with 0.1 mL of Mycobacterium butyricum in Incomplete Freund's Adjuvant (10 mg/mL). Either the vehicle (acidified saline, 1 mL/kg) or a compound of the invention (3, 10, or 30 mg/kg) is administered subcutaneously (b.i.d.), starting on the day following adjuvant immunization, and continued until the end of the experiment (N=10 rats per treatment group). Clinical scores (see below) are measured in all limbs 3 times per week throughout the study. Rats are euthanized 34–35 days after immunization. At the time of euthanasia, a radiologic evaluation (see below) of the hind paws is performed, a blood sample is collected for clinical blood chemistry and drug levels (high dose group only; 6 or 12 hours post final dose), a section of liver is obtained for measurement of potential toxicity, and the hind limbs are preserved for histopathological determination.

Clinical scoring—each limb is graded according to the following scale:

0 no signs of inflammation
1 moderate redness, first indication of swelling, joint flexible
2 moderate redness, moderate swelling, joint flexible
3 redness, significant swelling and distortion of the paw, joint beginning to fuse
4 redness, gross swelling and distortion of the paw, joint completely fused Radiological scoring—each hind limb is graded on a scale of 0–3 for each of the following parameters:

soft tissue swelling cartilage loss erosion heterotropic ossification

The compounds of the invention, when tested in this assay, demonstrate the ability to treat the arthritis present in the rats.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound selected from formula (I)

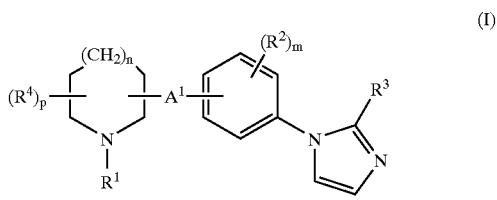

wherein:
n is 0 to 2;
m is 0 to 1;
p is 0 to 2;
$A^1$ is —O—, —$CH_2$O— or —N($R^6$)—;
$R^1$ is (1,3-benzodioxol-5-yl)alkyl (where the benzodioxolyl radical is optionally substituted by one or more substituents selected from the group consisting of alkyl, hydroxy, and alkoxy);

or $R^1$ is (1,3-benzodioxol-5-yl)carbonyl (where the benzodioxolyl radical is optionally substituted by one or more substituents selected from the group consisting of alkyl, hydroxy, and alkoxy):

$R^2$ is halo, haloalkyl, alkyl, or —$OR^6$;

$R^3$ is hydrogen or alkyl;

each $R^4$ is independently alkyl, halo, haloalkyl, hydroxy, alkoxy, amino, dialkylamino, monoalkylamino, nitro, carboxy, alkoxycarbonyl, aminocarbonyl, monoalkylaminocarbonyl, or dialkylaminocarbonyl; and $R^6$ is hydrogen or alkyl;

as a single stereoisomer, a mixture of stereoisomers, or as a racemic mixture of stereoisomers; or a pharmaceutically acceptable salt thereof.

2. The compound of claim 1 wherein:

n is 0;

m is 0 to 1;

p is 0 to 2;

$A^1$ is —O— or —$CH_2O$—;

$R^1$ is (1,3-benzodioxol-5-yl)alkyl (where the benzodioxolyl radical is optionally substituted by one or more substituents selected from the group consisting of alkyl, hydroxy, and alkoxy);

$R^2$ is halo, haloalkyl, alkyl, or —$OR^6$;

$R^3$ is hydrogen or alkyl;

each $R^4$ is independently alkyl, halo, haloalkyl, hydroxy, alkoxy, amino, dialkylamino, monoalkylamino, nitro, carboxy, alkoxycarbonyl, aminocarbonyl, monoalkylaminocorbonyl, or dialkylaminocarbonyl; and $R^8$ is hydrogen or alkyl.

3. The compound of claim 2 selected from the group consisting of the following compounds:

3-[4-(imidazol-1-yl)phenoxy]-1-[(1,3-benzodioxol-5-yl)methyl]pyrrolidine;

(3S)-3-[4-(imidazol-1-yl)phenoxy]-1-[(1,3-benzodioxol-5-yl)methyl]pyrrolidine;

(3R)-3-[4-(imidazol-1-yl)phenoxy]-1-[(1,3-benzodioxol-5-yl)methyl]pyrrolidine;

2-methoxycarbonyl-4-[4-(imidazol-1-yl)phenoxy]-1-[(1,3-benzodioxol-5-yl)methyl]pyrrolidine;

2-carboxy-4-[4-(imidazol-1-yl)phenoxy]-1-[(1,3-benzodioxol-5-yl)methyl]pyrrolidine; and 2-[(4-(imidazol-1-yl)phenoxy)methyl]-1-[(1,3-benzodioxol-5-yl)methyl]pyrrolidine.

4. The compound of claim 1 wherein:

n is 0;

m is 0 to 1;

p is 0 to 2;

$A^1$ is —O—; $R^1$ is (1,3-benzodioxol-5-yl)carbonyl (where the benzodaoxolyl radical is optionally substituted by one or more substituents selected from the group consisting of alkyl, hydroxy, and alkoxy);

$R^2$ is halo, haloalkyl, alkyl, or —$OR^6$;

$R^3$ is hydrogen or alkyl;

each $R^4$ is independently alkyl, halo, haloalkyl, hydroxy, alkoxy, amino, dialkylamino, monoalkylamino, nitro, carboxy, alkoxycarbonyl, aminocarbonyl, monoalkylaminocarbonyl, or dialkylaminocarbonyl; and $R^6$ is hydrogen or alkyl.

5. The compound of claim 4, namely, 3-[4-(imidazol-1-yl)phenoxy]-1-[(1,3-benzodioxol-5-yl)carbonyl]pyrrolidine.

6. The compound of claim 1 wherein:

n is 1 or 2;

m is 0 to 1;

p is 0 to 2;

$A^1$ is —O—, —$CH_2$—O— or —N(H)—;

$R^1$ is (1,3-benzodioxol-5-yl)alkyl (where the benzodioxolyl radical is optionally substituted by one or more substituents selected from the group consisting of alkyl, hydroxy, and alkoxy);

$R^2$ is halo, haloalkyl, alkyl, or —$OR^6$;

$R^3$ is hydrogen or alkyl;

each $R^4$ is independently alkyl, halo, haloalkyl, hydroxy, alkoxy, amino, dialkylamino, monoalkylamino, nitro, carboxy, alkoxycarbonyl, aminocarbonyl, monoalkylaminocarbonyl, or dialkylaminocarbonyl; and $R^6$ is hydrogen or alkyl.

7. The compound of claim 6 selected from the group consisting of the following compounds:

3-[4-(imidazol-1-yl)phenoxy]-1-[(1,3-benzodioxol-5-yl)methyl]piperidine;

(3S)-3-[4-(imidazol-1-yl)phenoxy]-1-[(1,3-benzodioxol-5-yl)methyl]piperidine;

(3R)-3-[4-(imidazol-1-yl)phenoxy]-1-[(1,3-benzodioxol-5-yl)methyl]piperidine;

2-[(4-(imidazol-1-yl)phenoxy)methyl]-1-[(1,3-benzodiaxol-5-yl)methyl]piperidine;

3-[(4-(imidazol-1-yl)phenoxy)methyl]-1-[(1,3-benzodioxol-5-yl)methyl]piperidine;

3-[(4-(imidazol-1-yl)phenyl)amino]-1-[(1,3-benzodioxol-5-yl)methyl]piperidine; and 3-[(4-(imidazol-1-yl)phenoxy]-1-[(1,3-benzodioxol-5-yl)methyl]hexahydro-1H-azepine.

8. A method of treating congestive heart failure, which method comprises administering to a mammal having congestive heart failure a therapeutically effective amount of a compound selected from the group consisting of the following formula:

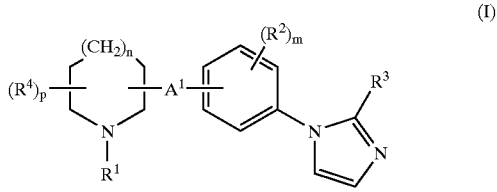

(I)

wherein:

n is 0 to 2;

m is 0 to 1;

p is 0 to 2;

$A^1$ is —O—,—$CH_2O$— or —$N(R^6)$—;

$R^1$ is (1,3-benzodioxol-5-yl)alkyl (where the benzodioxolyl radical is optionally substituted by one or more substituents selected from the group consisting of alkyl, hydroxy, and alkoxy);

or $R^1$ is (1,3-benzodioxol-5-yl)carbonyl (where the benzodioxolyl radical is optionally substituted by one or more substituents selected from the group consisting of alkyl, hydroxy, and alkoxy);

$R^2$ is halo, haloalkyl, alkyl, or —$OR^6$;

each $R^3$ is hydrogen or alkyl;

each $R^4$ is independently alkyl, halo, haloalkyl, hydroxy, alkoxy, amino, dialkylamino, monoalkylamino, nitro, carboxy, alkoxycarbonyl, aminocarbonyl, monoalkylaminocarbonyl, or dialkylaminocarbonyl; and R⁶ is hydrogen or alkyl;
as a single stereoisomer, a mixture of stereoisomers, or as a racemic mixture of stereoisomers; or a pharmaceutically acceptable salt thereof.

9. A pharmaceutical composition comprising a pharmaceutically acceptable excipient and a therapeutically effective amount of a compound selected from formula (I)

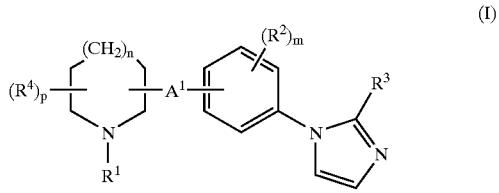

(I)

wherein:
n 0 to 2;
m is 0 to 1;
p is 0 to 2;
A¹ is —O—, —CH₂O— or —N(R⁶)—;
R¹ is (1,3-benzodioxol-5-yl)alkyl (where the benzodioxolyl radical is optionally substituted by one or more substituents selected from the group consisting of alkyl, hydroxy, and alkoxy);
or R¹ is (1,3-benzodioxol-5-yl)carbonyl (where the benzodioxolyl radical is optionally substituted by one or more substituents selected from the group consisting of alkyl, hydroxy, and alkoxy);
R² is halo, haloalkyl, alkyl, or —OR⁶;
each R³ is hydrogen or alkyl;
each R⁴ is independently alkyl, halo, haloalkyl, hydroxy, alkoxy, amino, dialkylamino, monoalkylamino, nitro, carboxy, alkoxycarbonyl, aminocarbonyl, monoalkylaminocarbonyl, or dialkylaminocarbonyl; and R⁶ is hydrogen or alkyl; as a single stereoisomer, a mixture of stereoisomers, or as a racemic mixture of stereoisomers; or a pharmaceutically acceptable salt thereof.

10. A pharmaceutical composition of claim 9 wherein:
n is 0;
m is 0 to 1;
p is 0 to 2;
A¹ is —O—, —CH₂O—;
R¹ is (1,3-benzodioxol-5-yl)alkl (where the benzodioxolyl radical is optionally substituted by one or more substituents selected from the group consisting of alkyl, hydroxy, and alkoxy);
R² is halo, haloalkyl, alkyl, or —OR⁶;
R³ is hydrogen or alkyl;
each R⁴ is independently alkyl, halo, haloalkyl, hydroxy, alkoxy, amino, dialkylamino, monoalkylamino, nitro, carboxy, alkoxycarbonyl, aminocarbonyl, monoalkylaminocarbonyl, or dialkylaminocarbonyl, and R⁶ is hydrogen or alkyl.

11. The phamiaceutical composition of claim 10 wherein the compound is selected from the group consisting of the following compounds:
3-[4-(imidazol-1-yl)phenoxy]-1-[(1,3-benzodioxol-5-yl)methyl]pyrrolidine;

(3S)-3-[4-(imidazol-1-yl)phenoxy]-1-[(1,3-benzodioxol-5-yl)methyl]pyrrolidine;
(3R)-3-[(4-(imidazol-1-yl)phenoxy]-1-[(1,3-benzodioxol-5-yl)methyl]pyrrolidine;
2-methoxycarbonyl-4-(imidazol-1-yl)phenoxy]-1-[(1,3-benzodioxol)-5-yl)methyl]pyrrolidine;
2-carboxy-4-[4-(imidazol-1-yl)phenoxy]-1-[(1,3-benzodioxol-5-yl)methyl]pyrrolidine; and
2-[(4-(imidazol-1-yl)phenoxy]methyl]-1-[(1,3benzodioxol-5-yl)methyl]pyrrolidine.

12. The pharmaceutical composition of claim 9 wherein:
n is 0;
m is 0 to 1;
p is 0 to 2;
A¹ is —O—;
R¹ is (1,3-benzodioxol-5-yl)carbonyl (where the benzodioxolyl radical is optionally substituted by one or more substituents selected from the group consisting of alkyl, hydroxy, and alkoxy);
R² is halo, haloalkyl, alkyl, or —OR⁶;
R³ is hydrogen or alkyl;
each R⁴ is independently alkyl, halo, haloalkyl, hydroxy, alkoxy, amino, dialkylamino, monoolkylamino, nitro, carboxy, alkoxycarbonyl, aminocarbonyl, monoalkylaminocarbonyl, or dialkylaminocarbonyl; and R⁶ is hydrogen or alkyl.

13. The pharmaceutical composition of claim 12 wherein the compound is 3-[4-(imidazol-1-yl)phenoxy]-1-[(1,3-benzodioxol-5-yl)carbonyl]pyrrolidine.

14. The pharmaceutical composition of claim 9 wherein
n is 1 or 2;
m is 0 to 1;
p is 0 to 2;
A¹ is —O—, —CH₂—O— or —N(H)—;
R¹ is (1,3-benzodioxol-5-yl)alkyl (where the benzodioxolyl radical is optionally substituted by one or more substituents selected from the group consisting of alkyl, hydroxy, and alkoxy);
R² is halo, haloalkyl, alkyl, or —OR⁶;
R³ is hydrogen or alkyl;
each R⁴ is independently alkyl, halo, haloalkyl, hydroxy, alkoxy, amino, dialkylamino, monoalkylamino, nitro, carboxy, alkoxycarbonyl, aminocarbonyl, monoalkylaminocarbonyl, or dialkylaminocarbonyl; and R⁶ is hydrogen or alkyl.

15. The pharmaceutical composition of claim 14 wherein the compound is selected from the group consisting of the following compounds:
3-[4-(imidazol-1-yl)phenoxy]-1-[(1,3-benzodioxol-5-yl)methyl]piperidine;
(3S)-3-[4-(imidazol-1-yl)phenoxy]-1-[(1,3-benzodioxol-5-yl)methyl]piperidine;
(3R)-3-[4-(imidazol-1-yl)phenoxy]-1-[(1,3-benzodioxol-5-yl)methyl]piperidine;
2-[(4-(imidazol-1-yl)phenoxy)methyl]-1-[(1,3-benzodioxol-5-yl)methyl]piperidine;
3-[4-(imidazol-1-yl)phenoxy)methyl]-1-[(1,3-benzodioxol-5-yl)methyl]piperidine;
3-[(4-(imidazol-1-yl)phenyl)amino]-1-[(1,3-benzodioxol-5-yl)methyl]piperidine; and
3-[4-(imidazol-1-yl)phenoxy]-1-[(1,3-benzodioxol-5-yl)methyl]hexahydro-1H-azepine.

* * * * *